(12) United States Patent
Chunlin

(10) Patent No.: US 7,820,391 B2
(45) Date of Patent: Oct. 26, 2010

(54) BASELESS NUCLEOTIDE ANALOGUES AND USES THEREOF

(75) Inventor: Tao Chunlin, Beverly Hills, CA (US)

(73) Assignee: Osmetech Molecular Diagnostics, Pasadena, CA (US)

( * ) Notice: Subject to any disclaimer, the term of this patent is extended or adjusted under 35 U.S.C. 154(b) by 44 days.

(21) Appl. No.: 12/266,414

(22) Filed: Nov. 6, 2008

(65) Prior Publication Data

US 2009/0155795 A1   Jun. 18, 2009

Related U.S. Application Data

(60) Provisional application No. 60/985,717, filed on Nov. 6, 2007.

(51) Int. Cl.
| | | |
|---|---|---|
| C12Q 1/68 | (2006.01) | |
| C07H 21/02 | (2006.01) | |
| C07H 21/04 | (2006.01) | |
| C07H 21/00 | (2006.01) | |
| C07H 19/04 | (2006.01) | |

(52) U.S. Cl. .................. 435/6; 536/23.1; 536/24.3; 536/25.3; 536/26.6; 422/61

(58) Field of Classification Search ............ 435/6; 536/23.1, 24.3, 25.3, 26.6; 422/61
See application file for complete search history.

(56) References Cited

U.S. PATENT DOCUMENTS

| 6,211,356 B1 | 4/2001 | Wiessler et al. |
| 2003/0143556 A1 | 7/2003 | Blackburn et al. |
| 2003/0232354 A1 | 12/2003 | Yu et al. |

FOREIGN PATENT DOCUMENTS

| WO | WO 86/05815 A | 10/1986 |
| WO | WO 01/06016 A | 1/2001 |
| WO | WO 02/20838 A | 3/2002 |
| WO | WO 03/055898 A | 7/2003 |

OTHER PUBLICATIONS

Kerman et al. "Peptide biosensors for the electrochemical measurement of protein kinase activity," *Analytical Chemistry* 80(24) (2008).
Lu et al. "Aptamer-based electrochemical sensors that are not based on the target binding-induced conformational change of aptamers," *The Analyst* 133(9):1256-1260 (2008).
Song et al. "Electrochemical detection of kinase-catalyzed phosphorylation using ferrocene-conjugated ATP," *Chemical Communication* 8(4):502-504 (2008).

*Primary Examiner*—Jezia Riley
(74) *Attorney, Agent, or Firm*—Morgan, Lewis & Bockius LLP; Robin M. Silva

(57) ABSTRACT

A method of detecting a target nucleic acid.

22 Claims, No Drawings

BASELESS NUCLEOTIDE ANALOGUES AND USES THEREOF

This application claims the benefit of U.S. Provisional Application Ser. No. 60/985,717 filed Nov. 6, 2007 under 35 U.S.C. §119, and is incorporated entirely herein by reference.

FIELD OF THE INVENTION

The present invention is directed to nucleotide analogues and uses thereof.

BACKGROUND OF THE INVENTION

The detection of specific nucleic acids is an important tool for diagnostic medicine and molecular biology research. Gene probe assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48-51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41-47 (1993)).

There is a variety of detection methods that have been developed to detect the product resulting from PCR amplification. Detection can be achieved directly by incorporating signal generating nucleotide analogues during the PCR reaction, or indirectly, e.g., such as by hybridization with nucleic acid probes having incorporated signal generating nucleotide analogues. In either approach, there is a need for having sensitive and stable nucleotide analogues, which ideally could be detected automatically. To that end, fluorescent tagging, with its advantages of high sensitivity and multicolor detection, had been developed and quickly came to dominate applications in nucleic acid sequencing and microarray expression analysis. A broad variety of fluorescent-tagged NTPs, dNTPs and ddNTPs are commercially available.

An alternative to fluorescence based detection is electrochemical detection ("ECD"), which can be highly sensitive, rapid and amenable to inexpensive production in miniaturized ("lab-on-a-chip") formats. Most electrochemical applications are based upon introducing one or more copies of a conjugated redox label, typically metal complexes, metallocenes or quinines. As with different fluor compounds, redox labels are also available that have different redox potentials, which makes them attractive candidates for multiplex nucleic acid detection and sequencing should they be sufficiently integrateable or conjugatable into a growing nucleic acid chain, synthetically or naturally.

One approach has been to use ferrocene or its derivatives as label agents. In this approach, ferrocene-containing labeling agents and oligonucleotides are synthesized separately. Then the ferrocene-containing labeling agent is used to end-label the oligos at either the 5' or 3' end. For example, see Brown et al., Metalloorganic labels for DNA sequencing and mapping, New Journal of Chemistry, 18:317-326 (1994).

In early demonstrations of ferrocene tagging, 5'-aminohexyl oligonucleotides were chemically conjugated with carboxyl derivatives of ferrocene to enable electrochemical detection ("ECD") of hybridization and PCR amplicons at femtomole levels. See Takenaka et al., Electrochemically active DNA probes: detection of target DNA sequences at fermtomole level by high-performance liquid chromatography with electrochemical detection, Analytical Biochemistry, 218: 436-443 (1994); Ihara et al., Ferrocene-oligonucleotide conjugates for electrochemical probing of DNA. Nucleic Acids Research 24: 4273-4278 (1996); and Uto et al., Electrochemical analysis of DNA amplified by the polymerase chain reaction with a ferrocenylated oligonucleotide, Analytical Biochemistry, 250: 122-124 (1997).

Such ferrocene labeling can also be used for internal labeling. Internal post-synthetic labeling of DNA probes has been obtained by reaction with ferrocene carboxaldehyde or aminoferrocene. See Xu et al., Electrochemical detection of sequence-specific DNA using a DNA probe labeled with aminoferrocene and chitosan modified electrode immobilized with ssDNA. Analyst, 126:62-65 (2001).

Alternatively, ferrocene labeling agent can be used for incorporation during chemical oligonucleotide synthesis. Ferrocene phosphoramidites and monomers with a ferrocenyl moiety linked to position 5 of 2'-dU or the 2'-sugar position of dA and dC have been described, as has on-column derivatization of iodo-dU with ferrocenyl propargylamide. See Wlassoff and King, Ferrocene conjugates of dUTP for enzymatic redox labelling of DNA, Nucleic Acids Research, 30:e58 (2002) and references therein, all expressly incorporated by reference.

For example, Navarro et al. developed bisfunctional ferrocene containing phosphoramidite and dimethoxytrityl ("DMT") group, and used them in an automated solid-phase DNA synthesizer using phosphoramidite chemistry. Navarro et al., Automated synthesis of new ferrocenyl-modified oligonucleotides: study of their properties in solution, Nucleic Acids Research, 32:5310-5319 (2004). However, such compounds have lower coupling yield. The A, T, C and G synthons classically reacted with an average coupling yield of 98% (measured via DMT quantification). In comparison, the coupling yield for the bifunctional ferrocene compound 2, as shown below, was 95% from DMT quantification, and the coupling yield of compound 1, also shown below, was even lower, estimated to be 80%. Such low coupling yield renders them inadequate for routine DNA synthesis.

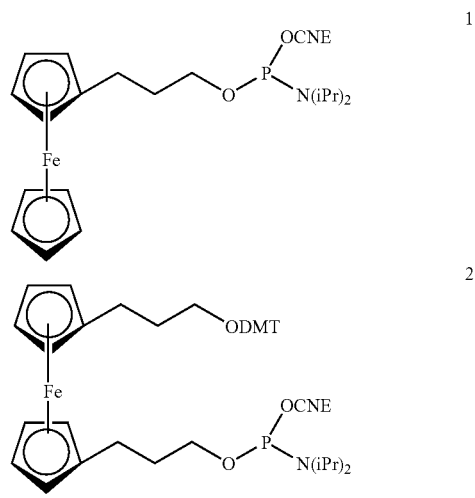

In routine automatic nucleic acids synthesis, high average stepwise yield is crucial. Coupling efficiency has dramatic effect on the overall yield, as illustrated in Table 1.

TABLE 1

The relationship between coupling efficiency and yield in DNA synthesis

| Oligonucleotide length | Coupling efficiency | | | | |
|---|---|---|---|---|---|
| | 90% | 95% | 97% | 98.5% | 99.5% |
| 10 mer | 38.7 | 63.0 | 76.0 | 87.3 | 95.6 |
| 20 mer | 13.5 | 37.7 | 56.1 | 75.0 | 90.9 |
| 50 mer | — | 8.10 | 22.5 | 47.7 | 78.2 |
| 100 mer | — | — | 4.90 | 22.4 | 60.88 |

As can be seen, the effect of coupling efficiency on the overall yield is much greater for longer sequence, and an average stepwise yield less than 98% is totally unacceptable for routine oligonucleotide synthesis. See Brown and Brown, Modern machine-aided methods of oligoxyribonucleotide synthesis, in Oligonucleotides and Analogues: A Practical Approach, Ed. Eckstein, IRL Press, Oxford UK (1991), herein expressly incorporated by reference. As such the available ferrocene derivatives, such as those reported by Navarro et al. are not useful in routine DNA synthesis.

There have also been attempts to develop ferrocene-containing nucleotide analogues for incorporation of ferrocene labels into DNA by polymerases. For such purpose, ferrocene-containing dUTPs were developed by tagging ferrocene to the 5 position of the base of dUTP. Such analogue could be incorporated as dTTP substitutes using different polymerases. However, such analogues only have rather low incorporation efficiency and lead to pre-mature termination. For example, in a PCR reaction, the analogues have to be doped with normal dTTP for chain growth. There was no amplicon obtained when only analogues were used. See Wlassoff and King, Ferrocene conjugates of dUTP for enzymatic redox labelling of DNA, Nucleic Acids Research, 30:e58 (2002) and references therein, all expressly incorporated by reference. It is unclear whether such analogues could result in coupling efficiency high enough for routine automated DNA synthesis. However, given the low incorporation efficiency demonstrated in polymerase synthesis, it is doubtful such analogues will have coupling efficiencies high enough for routine DNA synthesis. New analogues with higher coupling efficiency are therefore needed.

We previously described two such analogues, N6 and W97, which are ferrocene nucleosides. See US publications 20030232354 and 20030143556, each entitled "Nucleic acid reactions using labels with different redox potentials." However, the "bases" in those labels contribute to nonspecific binding background and regioisomers that are difficult to synthesize and purify, and that are unnecessary in end-labeling applications, where hybridization functionality is not necessarily needed. Moreover, when ferrocene is used as the label, hydrophobicity can be a problem.

It is an object of the invention to develop "baseless" labels conducive to lessening one or more of the above drawbacks.

SUMMARY OF THE INVENTION

The present invention provides "baseless" nucleotide analogues having relatively high coupling efficiency that are particularly useful in nucleic acid synthesis. The invention also provides compositions that include them and methods of making and using them.

In a first aspect the invention features an analog compound having formula (I):

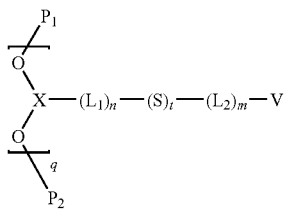

wherein X is a backbone spacer; S is a solubility moiety; t is 0 or 1; V is a label, preferably a redox active moiety (RAM); $L_1$ and $L_2$ are linkers; n=0 or 1; m=0 or 1; wherein n+m is at least 1; $P_1$ and $P_2$ are independently selected from the group consisting of hydrogen, phosphoramidite, a protecting group, and a nucleoside containing group; wherein at least one of $P_1$ and $P_2$ is said protecting group or said nucleoside containing group; and wherein q is greater than or equal to 1.

In a preferred embodiment the redox active moiety comprises a metallocene or metallocene derivative, preferably ferrocene or a ferrocene derivative. Preferably at least one of said protection groups $P_1$ or $P_2$ is dimethoxytrityl ("DMT"). Preferably the backbone spacer X is a $C_3$ alkyl group, substituted or unsubstituted. Aa preferred solubility moiety has formula:

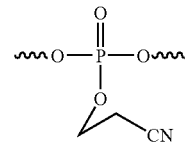

Preferably linkers $L_1$ and $L_2$ are $C_1$ alkyl and n is 1 and m is 4, although other linkers can be used as will be apparent to one of skill in the art. Preferably also, at least one of $P_1$ and $P_2$, is a nucleoside containing group.

A preferred compound of this aspect of the invention has formula (II):

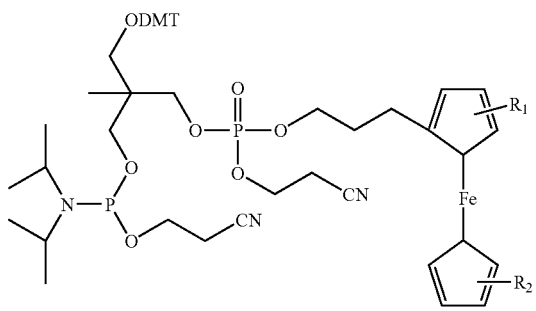

wherein $R_1$ and $R_2$ are independently selected from H and halogen. In one preferred embodiment, $R_1$ and $R_2$ are both H. In another preferred embodiment, $R_1$ is H and $R_2$ is Cl. In still another preferred embodiment, $R_1$ and $R_2$ are both Cl. An especially preferred compound has formula (III)

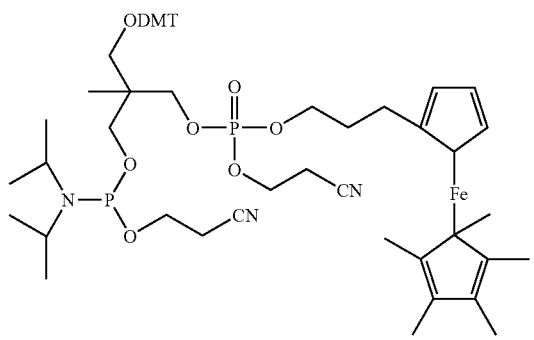

In another aspect, the invention features a nucleic acid derivative polymer comprising an analogue compound according to claim 1 having formula (IV):

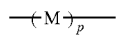

wherein p is 1 or greater; and M has formula (V):

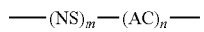

wherein NS is a nucleoside and AC is the integrated analogue compound; wherein m is 0 or greater; n is 0 or greater; when p is greater than 1, for each M, m and n could be different; and there is at least one NS and one AC.

In another aspect, the invention features a method of making a nucleic acid that comprises use of the compounds above in repetitive coupling; deprotecting; and extending steps on a resin to produce a nucleic acid chain containing the compound(s).

In another aspect, the invention features a method of detecting a target nucleic acid using the compounds and analogs above. In some embodiments, this contemplates "uniplexing"—where only one label is used and/or detected at a time. In other embodiments, such as in some embodiments of SNP detection, arrays and multiple different labels may be used and/or detected simultaneously, i.e., "multiplexing".

In preferred embodiments, the methods comprise providing a substrate having [an] electrode(s); a self-assembled monolayer (SAM) on said electrode(s); capture probe(s) disposed on said electrode(s), wherein said capture probe(s) bind(s) to said target nucleic acid(s); forming [a] complex(es) comprising said capture probe(s), said target nucleic acid(s), and [a] label probe(s) comprising the nucleic acid derivative(s) according to the preceding aspect/embodiments; and detecting electron transfer from [a] redox active moiety(ies) of said label probe(s) to said conductive surface of said electrode(s) to detect said target nucleic acid(s).

In embodiments where ferrocene or ferrocene derivatives are the label, those particular compounds are known as non-nucleotide ferrocene labels (NNFLs), which is clearer than the oxymoronic term, "baseless nucleotide."

In another aspect, the invention features a useful new compound, W330, which is particularly useful as a linker in 5' reverse capture probe syntheses.

Other aspects of the invention feature chemical intermediates and linkers as described below.

Still other aspects and embodiments contemplate sequencing applications using the compounds and methods of the preceding aspects and embodiments, which applications will be clear to one of skill in the art viewing this specification.

Still other aspects and embodiments of the invention will be apparent in the claims, figures, and discussion below.

BRIEF DESCRIPTION OF THE DRAWINGS

None.

DETAILED DESCRIPTION OF THE PREFERRED EMBODIMENTS

The present invention provides intermediates and analogues useful for detecting nucleic acid binding events, preferably although not necessarily electrochemically. DNA-based electrochemical biosensors combine nucleic acid layers with electrochemical transducers to provide a simple, accurate and inexpensive platform for patient diagnosis. For a general review, see Drummond et al., Electrochemical DNA sensors, Nature Biotechnology, 21:1192-1199 (2003). The electronic signal is generated due to the electrochemical response of labeling DNA with metal complexes or electroactive compounds. In this context, ferrocene has been particularly chosen because it has good stability and enables convenient chemical synthesis. There are different approaches to labeling nucleic acids with ferrocene, as discussed in the "Background" section, above. As will be apparent below, the analogues and methods of the invention afford one or more advantages over that background art.

Backbone Spacer

The nucleotide analogues of the invention comprise a backbone spacer. By "backbone spacer" is hereby meant a moiety that could be fit into the back bone structure of a nucleic acid to generate nucleic acid derivatives that can hybridize with complementary nucleic acids. To that end, the distance between the two oxygens preferably is similar to the orthogonal distance between two bases in a double stranded nucleic acid. Alternatively, the distance between the two oxygens can be several times the orthogonal distance between two bases in a normal double stranded (hybridized) nucleic acid.

Preferred backbone spacers include alkyl groups including heteroalkyl groups such as $(CH_2)n$ and $(CH_2CH_2O)n$, with n from 1 to 10 being preferred, and n=1 to 4 being especially preferred, and n=4 being particularly preferred.

The backbone spacer could also include an aromatic group. By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

In a preferred embodiment, the backbone spacer comprises a tert-butyl as depicted in representative Structure 1.

Structure 1

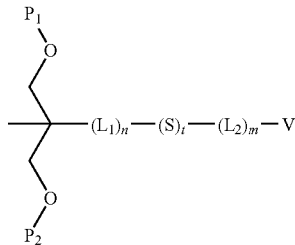

wherein S is a solubility moiety; t is 0 or 1; V is a label, preferably a redox active moiety (or redox active molecule) (RAM), electroactive moiety (EAM) or "electron transfer moiety" or "ETM"; $L_1$ and $L_2$ are linkers; n=0 or 1; m=0 or 1; wherein n+m is at least 1; $P_1$ and $P_2$ are independently selected from the group consisting of hydrogen, phosphoramidite, a protecting group, and a nucleoside containing group; wherein at least one of $P_1$ and $P_2$ is said protecting group or said nucleoside containing group; and wherein q is greater than or equal to 1

Thus, the nucleotide analogues may be incorporated into the backbone of a nucleic acid, as described in more detail below.

Solubility Moiety

One technical obstacle to using metallocene containing nucleotide analogues for detection of nucleic acids is that the yield for incorporation of metallocene containing nucleotide into nucleic acids is relative low. This is mainly due to the low solubility of the metallocene containing nucleotide analogues. Accordingly, in preferred embodiments the present invention provides nucleotide analogues comprising a solubility moiety. By "solubility moiety" or "SM", or grammar equivalents is meant a moiety or group that could affect the solubility of the nucleotide analogues. Preferably, the solubility moiety could increase the solubility of the nucleotide analogues.

There are a variety of groups that could serve as a solubility moiety, including but not limited to atoms or groups of atoms that can present a charge, e.g., phosphorus, sulfur, or nitrogen containing groups. In a preferred embodiment, the solubility moiety comprises phosphate, as depicted in representative structure 2.

Structure 2

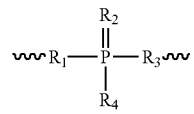

$R_1$ and $R_3$ could be conjugated bonds, preferably selected from acetylene (—C≡C—, also called alkyne or ethyne), alkene (—CH═CH—, also called ethylene), substituted alkene (—CR═CR—, —CH═CR— and —CR═CH—), amide (—NH—CO— and —NR—CO— or —CO—NH— and —CO—NR—), azo (—N═N—), esters and thioesters (—CO—O—, —O—CO—, —CS—O— and —O—CS—) and other conjugated bonds such as (—CH═N—, —CR═N—, —N═CH— and —N═CR—), (—SiH═SiH—, —SiR═SiH—, —SiR═SiH—, and —SiR═SiR—), (—SiH═CH—, —SiR═CH—, —SiH═CR—, —SiR═CR—, —CH═SiH—, —CR═SiH—, —CH═SiR—, and —CR═SiR—). Particularly preferred bonds are acetylene, alkene, amide, and substituted derivatives of these three, and azo. $R_1$ and $R_3$ could also be carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—), They could be the same or different.

$R_2$ and $R_4$ could be substitute groups. $R_2$ and $R_4$ could be carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). $R_2$ and $R_4$ could be the same or different.

In a preferred embodiment, the substitute groups comprise oxygen, as depicted in representative structure 3.

Structure 3

Linker

The solubility moiety could be linked to the backbone spacer directly, or indirectly via a linker. By "linker" is hereby meant any structure that could be used to link the solubility moiety and the backbone spacer. The linker also can link the solubility moiety to the label. Thus, in some embodiments, the linker between the backbone spacer and the solubility moiety is a first linker while the linker between the solubility moiety and label is a second linker. In some embodiments the linkers are the same. Preferred linkers include alkyl groups including heteroalkyl groups such as (CH$_2$)n and (CH$_2$CH$_2$O)n, with n from 1 to 10 being preferred, and n=1 to 4 being especially preferred, and n=4 being particularly preferred.

The linker could also comprise an aromatic group.

Alternatively, the linker is a conjugated bond, preferably selected from acetylene (—C≡C—, also called alkyne or ethyne), alkene (—CH═CH—, also called ethylene), substituted alkene (—CR═CR—, —CH═CR— and —CR═CH—), amide (—NH—CO— and —NR—CO— or —CO—NH— and —CO—NR—), azo (—N═N—), esters and thioesters (—CO—O—, —O—CO—, —CS—O— and —O—CS—) and other conjugated bonds such as (—CH═N—, —CR═N—, —N═CH— and —N═CR—), (—SiH═SiH—, —SiR═SiH—, —SiR═SiH—, and —SiR═SiR—), (—SiH═CH—, —SiR═CH—, —SiH═CR—, —SiR═CR—, —CH═SiH—, —CR═SiH—, —CH═SiR—, and —CR═SiR—). Particularly preferred bonds are acetylene, alkene, amide, and substituted derivatives of these three, and azo. The linker could also be carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—).

The aromatic group may be substituted with a substitution group, generally depicted herein as R. R groups may be added to 1) alter the solubility of the nucleotide analogue; and/or 2) alter redox potential of the redox active moiety, as described in more details in this application.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —NH$_2$, —NHR and —NR$_2$ groups, with R being as defined herein.

By "nitro group" herein is meant an —NO$_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—(CH$_2$)$_2$CH$_3$ and —O—(CH$_2$)$_4$CH$_3$ being preferred.

By "ester" herein is meant a —COOR group.

By "halogen" herein is meant bromine, iodine, chlorine, or fluorine. Preferred substituted alkyls are partially or fully halogenated alkyls such as CF$_3$, etc.

By "aldehyde" herein is meant —RCOH groups.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —(O—CH$_2$—CH$_2$)$_n$— group, although each carbon atom of the ethylene group may also be singly or doubly substituted, i.e. —(O—CR$_2$—CR$_2$)$_n$—, with R as described above. Ethylene glycol derivatives with other heteroatoms in place of oxygen (i.e. —(N—CH$_2$—CH$_2$)$_n$— or —(S—CH$_2$—CH$_2$)$_n$—, or with substitution groups) are also preferred.

Preferred substitution groups include, but are not limited to, methyl, ethyl, propyl, alkoxy groups such as —O—(CH$_2$)$_2$CH$_3$ and —O—(CH$_2$)$_4$CH$_3$, ethylene glycol and substituted derivatives of each of these.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

Redox Active Moiety

In preferred embodiments, the present invention provides nucleotide analogues that could be used for electrochemical detection. As such, the nucleotide analogues comprise a redox active moiety.

In one preferred embodiment, the nucleotide analogues comprise a redox active moiety. By "redox active moiety" or "RAM" or "redox active molecule" or "electron transfer moiety" or "ETM" herein is meant a compound which is capable of reversibly, semi-reversibly, or irreversibly transferring one or more electrons. The terms "electron donor moiety", "electron acceptor moiety", and "electron transfer moieties" or grammatical equivalents herein refer to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to synthesize a number of different redox active compounds. Preferred electron transfer moieties include, but are not limited to, transition metal complexes, organic electron transfer moieties, and electrodes.

In a preferred embodiment, the electron transfer moieties are transition metal complexes. The complex could have different structures. Structure 11 is a representative structure.

Structure 11

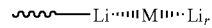

In the structure depicted here, M is a metal ion, with transitional metals being preferred. Transition metals include those whose atoms have a partial or complete d shell of electrons; elements having the atomic numbers 21-30, 39-48, 57-80 and the lanthanide series. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinum (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinum, cobalt and iron.

The transition metals are complexed with a variety of ligands, generally depicted herein as "Li", to form suitable transition metal complexes, as is well known in the art. Li are co-ligands, which provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the Li from the terminus of the conductive oligomer, the Li contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as $Li_m$). Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c] phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam), EDTA, EGTA and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergamon Press, 1987, Chapters 13.2 (pp. 73-98), 21.1 (pp. 813-898) and 21.3 (pp. 915-957), all of which are hereby expressly incorporated by reference.

Suitable sigma donating ligands using carbon, oxygen, sulfur and phosphorus are known in the art. For example, suitable sigma carbon donors are found in Cotton and Wilkinson, Advanced Inorganic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkinson.

The oxygen, sulfur, phosphorus and nitrogen-donating ligands are attached in such a manner as to allow the heteroatoms to serve as coordination atoms.

In a preferred embodiment, organometallic ligands are used. In addition to purely organic compounds for use as redox active moieties, and various transition metal coordination complexes with δ-bonded organic ligand with donor atoms as heterocyclic or exocyclic substituents, there is available a wide variety of transition metal organometallic compounds with n-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion $[C_5H_5(-1)]$ and various ring substituted and ring fused derivatives, such as the indenylide (−1) ion, that yield a class of bis (cyclopentadieyl) metal compounds, (i.e. the metallocenes); see for example Robins et al., J. Am. Chem. Soc. 104:1882-1893 (1982); and Gassman et al., J. Am. Chem. Soc. 108: 4228-4229 (1986), incorporated by reference. Of these, ferrocene $[(C_5H_5)_2 Fe]$ and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox active moieties.

Other potentially suitable organometallic ligands include cyclic arenes such as benzene, to yield bis(arene) metal compounds and their ring substituted and ring fused derivatives, of which bis(benzene)chromium is a prototypical example, Other acyclic π-bonded ligands such as the allyl(−1) ion, or butadiene yield potentially suitable organometallic compounds, and all such ligands, in conjunction with other π-bonded and δ-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox active moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkinson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, being either nitrogen donating ligands or metallocene ligands, or a mixture. These combinations are depicted in representative structures in Structures 12 (using phenanthroline as representative ligand), 13 (using cyclopentadienyl as representative ligands) and 14 (using ferrocene as the metal-ligand combination). The proper structure of ferrocene is Structure 12

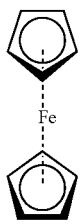

and all drawings contained herein wherein an iron atom is shown between or attached to two cyclopentadienyl rings shall be interpreted consistently with this, e.g., Structure 14 and the structures found in paragraphs 21, 83, 85, the examples and the claims.

Structure 13

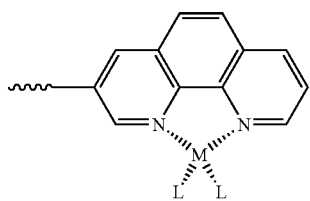

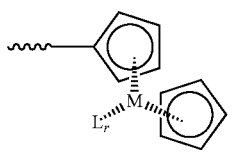

Structure 14

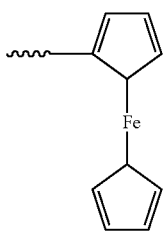

In a preferred embodiment, the ligands used in the invention show altered fluorescent properties depending on the redox state of the chelated metal ion. As described below, this thus serves as an additional mode of detection of electron transfer between the redox active moieties and the electrode.

In addition to transition metal complexes, other organic electron donors and acceptors may be used as redox active moieties. These organic molecules include, but are not limited to, riboflavin, xanthene dyes, azine dyes, acridine orange, N,N'-dimethyl-2,7-diazapyrenium dichloride ($DAP^{2+}$), methylviologen, ethidium bromide, quinones such as N,N'-dimethylanthra(2,1,9-def:6,5,10-d'e'f')diisoquinoline dichloride ($ADIQ^{2+}$); porphyrins ([meso-tetrakis(N-methyl-x-pyridinium)porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5,5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and substituted derivatives of these compounds.

In one embodiment, the electron donors and acceptors are redox proteins as are known in the art. However, redox proteins in many embodiments are not preferred.

It is also desirable in some instances to add additional substituent groups to one or both of the aromatic rings of the metallocene (or RAM). For example, as these nucleoside replacements are generally part of probe sequences to be hybridized with a substantially complementary nucleic acid, for example a target sequence or another probe sequence, it is possible to add substitutent groups to the metallocene rings to facilitate hydrogen bonding to the base or bases on the opposite strand. These may be added to any position on the metallocene rings. Suitable substituent groups include, but are not limited to, amide groups, amine groups, carboxylic acids, and alcohols, including substituted alcohols. In addition, these substitutent groups can be attached via linkers as well, although in general this is not preferred.

The redox active moiety could be linked to the backbone spacer directly or indirectly via a linker. Alternatively, when the analogue compound also contains a solubility moiety, the redox active moiety could be linked to the solubility moiety directly, or indirectly via a linker. The linker could be the kind of linkers described above.

In a preferred embodiment, the linker is 4 to 6 atoms, with preferably 3 atoms.

In addition, substituent groups on a RAM, particularly metallocenes such as ferrocene, may be added to alter the redox properties of the RAM. Thus, for example, in some embodiments, as is more fully described below, it may be desirable to have different RAMs attached in different, on different probes, or for different purposes (for example, calibration or as an internal standard). Thus, the addition of substituent groups on the metallocene may allow two different RAMs to be distinguished.

Alternatively, the redox properties of an RAM could be altered by adding different groups to the linker that linked the RAM to other parts of the analogue, such as the linker between the RAM and the SM. A variety of groups could be used to alter the redox properties of an RAM, as is known in the art.

Protecting Groups

The analogue compounds as provided in the instant invention also comprise, in some aspects and embodiments, protection groups, which are generally suitable for use in nucleic acid synthesis, with DMT, MMT and TMT all being preferred.

In a preferred embodiment, the analogue compounds have the formula (II):

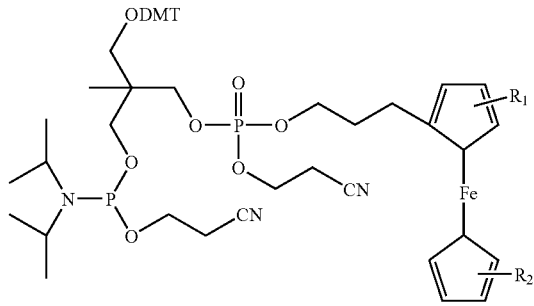

wherein $R_1$ and $R_2$ could be the same or different and are selected from hydrogen and halogen.

In another preferred embodiment, the analogue compound has the formula (III):

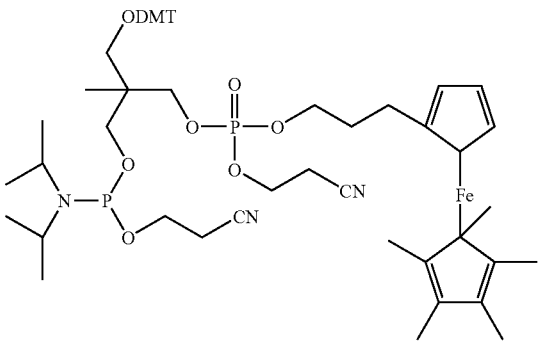

Intermediate Compounds

In order to generate these metallocene-backbone nucleic acid analogs, the intermediate components are also provided. Thus, in a preferred embodiment, the invention provides phosphoramidite metallocenes, as generally depicted in Structure 15:

Structure 15

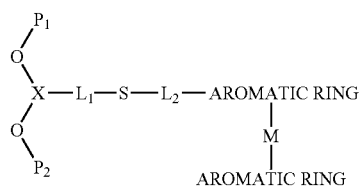

In structure 15, $P_1$ and $P_2$ are protection groups, generally suitable for use in nucleic acid synthesis, with DMT, MMT and TMT all being preferred. The aromatic rings can either be the rings of the metallocene, or aromatic rings of ligands for transition metal complexes or other organic ETMs. The aromatic rings may be the same or different, and may be substituted as discussed herein.

Structure 16

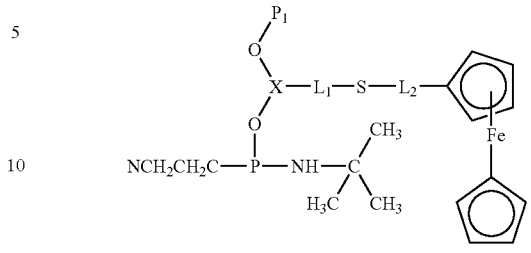

Nucleic Acid Derivative Comprising the Nucleotide Analogue(s)

The instant invention also provides nucleic acids comprising one or more of the nucleotide analogues as described herein.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of RAMs or conductive oligomers, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or RAM attachment, an analog structure may be used. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration. This is particularly advantageous in the systems of the present invention, as a reduced salt hybridization solution has a lower Faradaic current than a physiological salt solution (in the range of 150 mM).

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The instant invention also provides nucleic acids comprising analogue nucleotides as described herein. As described above, it is important to properly select the backbone of the nucleotide analogues so that after incorporating into nucleic acids, the nucleotide analogues will function like a nucleoside replacement, not disturbing the structure of the nucleic acids. This is especially important if the nucleic acids are used to form higher order structures, such as forming base-pairing to become double stranded DNA, double stranded RNA, or DNA-RNA hybrid duplexes. It may be less important if the nucleic acid is primarily used single stranded. However, if the single stranded nucleic acid needs to fold properly to be functional, such as being used as an apatmer or ribozyme, then it is crucial not to minimize the distortion of the nucleic acids structure.

A nucleic acid with nucleotide analogues incorporated is depicted in representative structure 17.

Structure 17

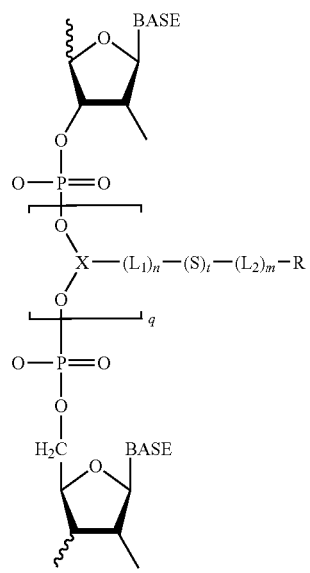

When the backbone spacer is three atoms long, its length would be very similar to the backbone being replaced and thus leads to minimum disruption to the overall nucleic acid structure, as depicted in Structure 18.

Structure 18

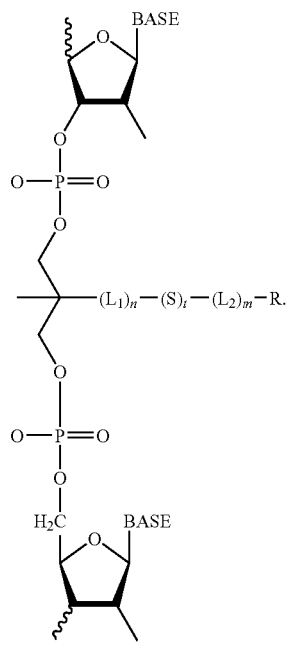

The nucleoside analogues can be synthesized as described below.

Once the nucleoside analogues are prepared, protected and activated, they may be incorporated into a growing oligonucleotide by standard synthetic techniques (Eckstein, Ed., Oligonucleotides and Analogues: A Practical Approach, IRL Press, Oxford, UK 1991) in several ways. In one embodiment, one or more nucleoside analogues are converted to the triphosphate form and incorporated into a growing oligonucleotide chain by using standard molecular biology techniques such as with the use of the enzyme DNA polymerase I, T4 DNA polymerase, T7 DNA polymerase, Taq DNA polymerase, reverse transcriptase, and RNA polymerases.

For the incorporation of a 3' modified nucleoside analogue to a nucleic acid, terminal deoxynucleotidyltransferase may be used. (Ratliff, Terminal deoxynucleotidyltransferase. In The Enzymes, Vol 14A. P. D. Boyer ed. pp 105-118. Academic Press, San Diego, Calif. 1981). Alternatively, and preferably, the amino nucleoside analogue is converted to the phosphoramidite or H-phosphonate form, which is then used in solid-phase or solution syntheses of oligonucleotides. In this way the nucleoside analogue, either for attachment at the ribose (i.e. amino- or thiol-modified nucleosides) or the base, is incorporated into the oligonucleotide at either an internal position or the 5' terminus. This is generally done in one of two ways. First, the 5' position of the ribose is protected with 4',4-dimethoxytrityl (DMT) followed by reaction with either 2-cyanoethoxy-bis-diisopropylaminophosphine in the presence of diisopropylammonium tetrazolide, or by reaction with chlorodiisopropylamino 2'-cyanoethyoxyphosphine, to give the phosphoramidite as is known in the art; although other techniques may be used as will be appreciated by those in the art. See Eckstein, supra; Caruthers, Science 230:281 (1985), both of which are expressly incorporated herein by reference.

The growing nucleic acid chain may also comprise at least one nucleoside analogue with a covalently attached second electron transfer moiety. As described herein, nucleoside analogues with covalently attached second electron transfer moieties may be made, and incorporated into the nucleic acid as outlined above. When a transition metal complex is used as the second electron transfer moiety, synthesis may occur in several ways. In a preferred embodiment, the ligand(s) are added to a nucleoside analogue, followed by the transition metal ion, and then the nucleoside analogue with the transition metal complex attached is added to an oligonucleotide, i.e. by addition to the nucleic acid synthesizer. Alternatively, the ligand(s) may be attached, followed by incorporation into a growing oligonucleotide chain, followed by the addition of the metal ion.

The nucleotide analogues can be added to either the 5' end or 3' end of the nucleic acids, or incorporated into the internal of the nucleic acids. The nucleotide analogues could be incorporated into different positions of the chain, either randomly or forming certain patterns. For example, several nucleotide analogues can be incorporated in a row. Or the nucleotide analogues can be incorporated in every other position, separated by normal nucleosides. In general, the nucleic acid derivative polymer generated by incorporating nucleotide analogues has formula (IV):

wherein p is 1 or greater; and M having formula (V):

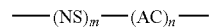

wherein NS is a nucleoside; AC is a said analogue compound; m is 0 or greater; n is 0 or greater; when p is greater than 1, for each M, m and n could be different; and there is at lest one NS and one AC.

In one embodiment, the nucleoside analogues are made with transition metal ligands, incorporated into a nucleic acid, and then the transition metal ion and any remaining necessary ligands are added as is known in the art. In an alternative embodiment, the transition metal ion and additional ligands are added prior to incorporation into the nucleic acid.

Method of Nucleotide Analogue Synthesis

The nucleotide analogues provided in the instant invention could be synthesized using approaches generally well known in the art. The instant invention provides exemplary synthesis schemes below.

Illustrative Detection Schemes Using the Nucleic Acid Analogues of the Invention Depending on the nature of the specific label used, detection can be, e.g., spectrophotometric, densitometric, radiometric, fluorimetric, or electrochemical, which procedures are well known in the art. For example, fluorimetric determinations can be done, e.g., according to Wohlstadter et al., U.S. Pat. No. 6,090,545, and electrochemical detection can be done, e.g., according to Kayyem et al. commonly-owned U.S. Pat. Nos. 6,221,583, 7,056,669 and 2002-0009810 A1, which are incorporated herein by reference.

Illustrative Specific Applications

The compositions of the present invention may be used in a variety of research, clinical, quality control, or field test settings. Single nucleotide polymorphism (SNP) testing is but one general research or clinical embodiment that can be used. Others will be apparent to the person of ordinary skill in the art.

In a preferred embodiment, the probes are used in genetic or pharmacogenetic diagnosis. For example, probes can be made using the techniques disclosed herein to detect target sequences associated with cancers (e.g., colon, breast (e.g., BRCA1) and P53 associated), Alzheimer's disease (e.g., the Apo E4 gene), cystic fibrosis, and any others diseases having a defined genetic basis. Warfarin/Coumadin® metabolism is one example of pharmacogenetic testing that can be done.

In an additional embodiment, infectious disease testing is facilitated, e.g., viral and bacterial detection, using the compounds and methods of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clamydia and other sexually transmitted diseases, may also be detected, for example using ribosomal RNA (rRNA) as the target sequences.

In a preferred embodiment, the nucleic acids of the invention find use as probes for toxic bacteria in the screening of water and food samples. For example, samples may be treated to lyse the bacteria to release its nucleic acid (particularly rRNA), and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

Thus, the present invention provides for extremely specific and sensitive probes, which may, in some embodiments, detect target sequences without removal of unhybridized probe. This will be useful in the generation of automated gene probe assays.

Alternatively, the compositions of the invention are useful to detect successful gene amplification in PCR, thus allowing successful PCR reactions to be an indication of the presence or absence of a target sequence. PCR may be used in this manner in several ways. For example, in one embodiment, the PCR reaction is done as is known in the art, and then added to a composition of the invention comprising the target nucleic acid with a ETM, covalently attached to an electrode via a conductive oligomer with subsequent detection of the target sequence. Alternatively, PCR is done using nucleotides labeled with an ETM, either in the presence of, or with subsequent addition to, an electrode with a conductive oligomer and a target nucleic acid. Binding of the PCR product containing ETMs to the electrode composition will allow detection via electron transfer. Finally, the nucleic acid attached to the electrode via a conductive polymer may be one PCR primer, with addition of a second primer labeled with an ETM. Elongation results in double stranded nucleic acid with a ETM and electrode covalently attached. In this way, the present invention is used for PCR detection of target sequences.

In a preferred embodiment, the arrays are used for mRNA detection. A preferred embodiment utilizes either capture probes or capture extender probes that hybridize close to the 3' polyadenylation tail of the mRNAs. This allows the use of one species of target binding probe for detection, i.e. the probe contains a poly-T portion that will bind to the poly-A tail of the mRNA target. Generally, the probe will contain a second portion, preferably non-poly-T, that will bind to the detection probe (or other probe). This allows one target-binding probe to be made, and thus decreases the amount of different probe synthesis that is done.

In a preferred embodiment, the use of restriction enzymes and ligation methods allows the creation of "universal" arrays. In this embodiment, monolayers comprising capture probes that comprise restriction endonuclease ends. By utilizing complementary portions of nucleic acid, while leaving "sticky ends", an array comprising any number of restriction endonuclease sites is made. Treating a target sample with one or more of these restriction endonucleases allows the targets to bind to the array. This can be done without knowing the sequence of the target. The target sequences can be ligated, as desired, using standard methods such as ligases, and the target sequence detected, using either standard labels or the methods of the invention.

The present invention provides methods which can result in sensitive detection of nucleic acids. In a preferred embodiment, less than about $10 \times 10^6$ molecules are detected, with less than about $10 \times 10^5$ being preferred, less than $10 \times 10^4$ being particularly preferred, less than about $10 \times 10^3$ being especially preferred, and less than about $10 \times 10^2$ being most preferred. As will be appreciated by those in the art, this assumes a 1:1 correlation between target sequences and reporter molecules; if more than one reporter molecule (i.e. electron transfer moiety) is used for each target sequence, the sensitivity will go up.

While the limits of detection are currently being evaluated, based on the published electron transfer rate through DNA, which is roughly $1 \times 10^6$ electrons/sec/duplex for an 8 base pair separation (see Meade et al., Angw. Chem. Eng. Ed., 34:352 (1995)) and high driving forces, AC frequencies of about 100 kHz should be possible. As the preliminary results show, electron transfer through these systems is quite efficient, resulting in nearly $100 \times 10^3$ electrons/sec, resulting in potential femtomole amp sensitivity for very few molecules.

Kits

In addition to the methods outlined herein, the invention further provides compositions, generally kits, useful in the practice of the invention. The kits include the compositions including the primers and enzymes, along with any number of reagents or buffers, including additional enzymes and primers, dNTPs and/or NTPs (including substituted nucleotides), buffers, salts, inhibitors, etc. The kits can optionally include instructions for the use of the kits.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. Applicants also note U.S. application Ser. Nos. 10/746,904, 09/621,275 (U.S. Pat. No. 6,686,150), Ser. No. 09/238,351 (U.S. Pat. No. 7,090,804), Ser. Nos. 09/626,096, 09/993,342 (U.S. Pat. No. 7,172,897), Ser. No. 09/760,384 (U.S. Pat. No. 7,312,087), and WO 98/20162, each of which is expressly incorporated herein by reference. In addition, all references cited herein are incorporated by reference in their entirety.

EXAMPLES

All chemicals noted below are commercially available through common vendors, e.g., Sigma-Aldrich (St. Louis, Mo., USA), or readily producible by those of skill in the art from common starting reagents or by reading this specification. Equipment used was as follows.

| Equipment Name | Manufacturer & Model |
|---|---|
| GC | Agilent 6890 Series GC System |
| MS | Agilent 5973 N. Mass Selective Detector |
| NMR | GE QE-300 |
| Electrospray Mass | HP 1100 MD |
| HPLC | Waters 2695 and Hitachi L-7200 |
| Capillary Electrophoresis | Beckman Pace MDQ |
| DNA/RNA Synthesizer | ABI 394 |

Example 1

Synthesis of Non-Nucleotide Ferrocene Label W370 and Intermediates

W370 has been identified as a Non-Nucleotide Ferrocene Label (NNFL) with a redox potential at ~−10 mV vs. a reference Ag/AgCl electrode. This label can be incorporated into oligonucleotides to make signal probes for OMD's eSensor® DNA detection system or any other ECD based system. We have developed procedures for the syntheses of W370 as indicated in Scheme 1 and Scheme 2 of Example 1 below, and have verified them by the production of three batches of desired compound.

W370 Synthesis Overview

Synthesis of intermediate W363 is shown in Scheme 1. Synthesis of W370 from W363 is shown in Scheme 2.

Scheme 1

Synthesis of W363

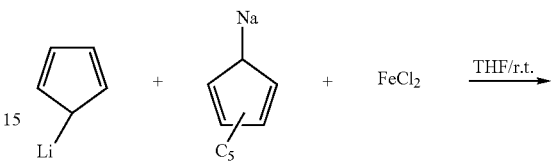

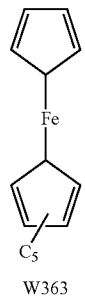

W363

Scheme 2

Synthesis of W370 from W363

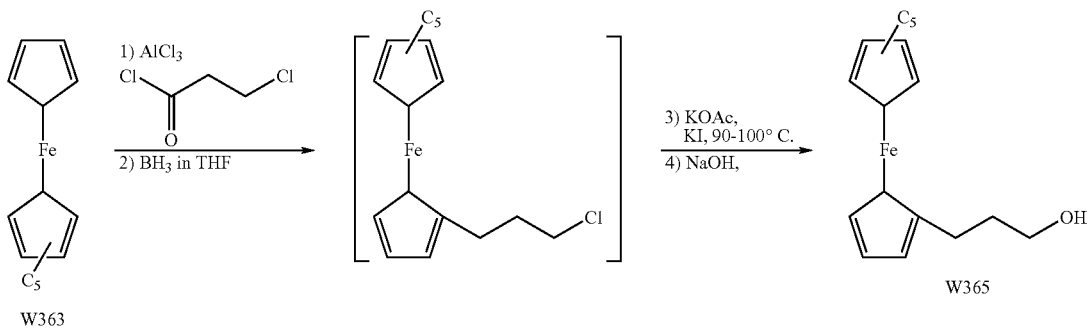

W365

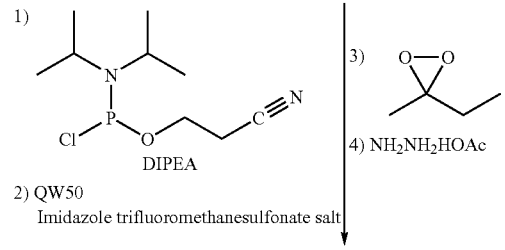

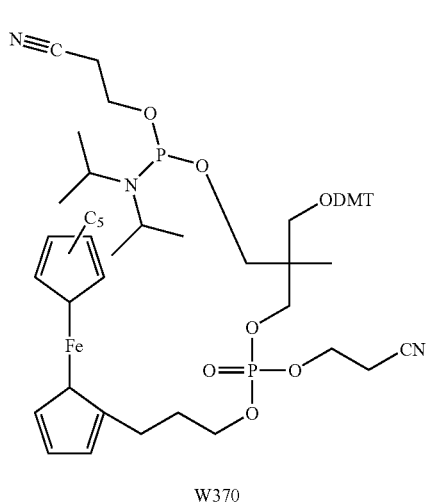

W370

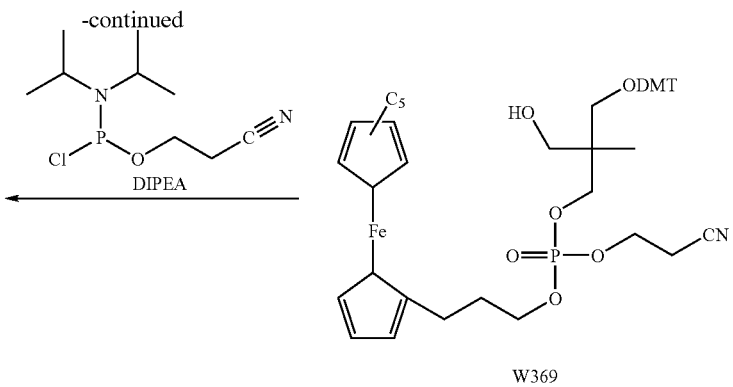

W369

Details of Synthesis of Intermediate W363

To a flame-dried round bottom flask equipped with a stirring bar was transferred lithium cyclopentadienylide (5.00 g, 69 mmol) under Argon, followed by sodium pentamethylcyclopentadienylide solution (147.2 ml, 74 mmol), then followed by ferrous chloride (9.75 g, 77 mmol). The mixture was stirred very slowly at room temperature for at least 24 h until all visible ferrous chloride solid at the bottom of the flask was consumed. Under vigorous stirring, 300 ml of hexane was added slowly into the reaction container. The mixture was allowed to settle down, and the clear solution was decanted from suspension at the bottom of the flask. The process was repeated until the top hexane layer was almost colorless. The combined solution was filtered through a 2-inch silica gel pad, packed with 3% TEA in hexane, and the column was eluted by hexane until the eluent was colorless. The hexane solution was concentrated under reduced pressure, and was then dried under high vacuum. The resultant solid was dissolved in a minimum amount of hot acetone, and was allowed to cool to room temperature. The bright yellow crystals are byproduct decamethylferrocene. The byproduct was filtered, and was washed by cold acetone. The mother liquid was concentrated under reduced pressure, and dried under vacuum. The resultant solid was dissolved in minimum amount of boiling MeOH, and was allowed to cool to room temperature. The resultant crystals are desired W363 and byproduct ferrocene, and they were filtered and washed by cold MeOH. After air-dry, transfer the solid to a round-bottom flask equipped with a 20/24 adapter and connecting to high vacuum. Submerge the whole flask in a water bath. The temperature of the water bath should be maintained between 28-35° C. The red-dark ferrocene was sublimed and collected at the adaptor. By using clean adaptors repeatedly, ferrocene was removed until only yellow crystals were collected on the adaptor. The solid again was dissolved in a minimum amount of hot acetone. It was allowed to cool down to room temperature, and filtered. The solid was washed by cold acetone. The resultant solution was concentrated under reduced pressure. The product was further dried under high vacuum to obtain constant weight. W363 was obtained as brown/yellowish powder. GC/MS: retention time: 11.76 minutes; W363 purity: >90%, residual ferrocene: <5%. M/e: 256 (M$^+$, 100), 199 (25), 121 (20). $^1$H-NMR (300 MHz, DMSO-d$_6$): δ3.65 (s, 5H, Cp), 1.87 (s, 15H, 5C$\underline{H}_3$).

Details of Synthesis of Intermediate W365

A solution of W363 (10.25 g, 40 mmol) in 100 mL anhydrous dichloromethane was cooled in an ice water bath for 15 to 20 minutes. A clear solution of 3-chloropropionyl chloride (4.90 mL, 52.7 mmol) and ACl$_3$ (6.67 g, 49.4 mmol) in 30 mL anhydrous dichloromethane was prepared in a separate flask, cannulated into the reaction vessel within 2 minutes. The mixture was stirred in the ice bath for additional 3 to 13 min at 0° C. The color of the reaction mixture was turned to bright purple, which is typical in a Friedal-Crafts reaction. Borane in THF (60.00 mL of 1 M solution in THF, 60 mmol) was added slowly at 0° C. After stirring at room temperature for 40 to 45 min, the mixture was cooled to 0° C. in an ice/water bath. A total of 40 mL of TEA was added slowly. The mixture was transferred to a beaker with ice/water with vigorous stirring, and 150 mL of DCM were used to rinse the flask. The solution was added to the beaker. The mixture was transferred into a separation funnel. The organic layer was separated, and the aqueous phase was extracted by 3×100 mL of DCM. The organic solution was combined, diluted with 400 mL of hexane and then washed by water (3×100 mL), dried with anhydrous sodium sulfate and concentrated under reduced pressure until no visible gas development was observed. To the residue was added 100 mL of N,N-Dimethylformamide, potassium acetate (9.82 g, 99.8 mmol) and potassium iodide (9.95 g, 60.2 mmol). The mixture was heated and stirred at 95+/−5° C. for 60 to 70 minutes. After being cooled to room temperature, it was filtered through a Celite-pad. 100 ml of DMF was used to rinse the Celite pad. 50 mL of 4M NaOH solution was added to the reaction mixture, and it was stirred at room temperature for 60 to 70 minutes, and 200 ml of water was added. The mixture was extracted with three portions of 50% ethyl acetate in hexanes (3×150 mL). The combined organic layer was washed three times by water (3×150 mL), dried with anhydrous sodium sulfate and concentrated. After column chromatography on silica gel (silica gel: 150 g; eluting solvents: 1% ethyl acetate in hexane (1 L); 5% ethyl acetate in hexane (1 L); 30% ethyl acetate in hexane (1.5 L), W365 was recovered as orange-colored viscous liquid. MS; m/e: 314 (M$^+$, 100), 199 (25), 121 (20). $^1$H-NMR (300 MHz, DMSO-d$_6$): δ4.34 (t, J=5.4 Hz, 1H, O$\underline{H}$), 3.56-3.50 (d, 4H, Fc-$\underline{H}$), 3.38 (m, 2H, C$\underline{H}_2$—OH), 2.16 (m, 2H, C$\underline{H}_2$-Fc), 1.46 (s, 15H, 5C$\underline{H}_3$), 1.50 (m, 2H, C$\underline{H}_2$).

Details of Synthesis of Intermediate W369

To a solution of W365 (9.00 g, 28.6 mmol) in 72.0 mL anhydrous dichloromethane was added N,N-diisopropylethylamine (6.6 mL, 37.6 mmol) and the mixture was cooled to 0° C. After addition of N,N-Diisopropylethylamino cyanoethyl phosphoramidic chloride (6.84 ml, 30.5 mmol) at 0° C., the mixture was stirred at room temperature for 60 to 70 minutes. QW50 (18.00 g, 34.6 mmol) in 90 mL anhydrous dichloromethane was added, followed by addition of imidazole trifluoromethane-sulfonate salt (8.14 g, 37.5 mmol) in 30 mL of acetonitrile. After stirring at room temperature for 60 to 70 minutes, the mixture was cooled to 0° C. for 15 to 20 min. A solution of 2-butanone peroxide (8.50 mL of 3.6 M solution, 30.6 mmol) in 120 mL anhydrous dichloromethane was cooled at 0° C. for 15 to 20 min, and added to the reaction flask. The reaction was stirred at 0° C. for exactly 2 minutes. Hydrazine acetate (13.23 g, 143.6 mmol) in 90 mL methanol was added and the reaction was stirred at room temperature for 60 to 70 minutes. The organic layer was extracted by water and 5% sodium bicarbonate, then dried over anhydrous sodium sulfate and concentrated. After being loaded on a short column packed with 150 g silica gel in 0.5% DIPEA in EtOAc, the crude product was eluted in EtOAc, and concentrated. The crude product was loaded to another column (silica gel: 200 g in 0.5% DIPEA/25% ethyl acetate in hexane), eluted with 50% ethyl acetate in hexanes (1 L); 75% ethyl acetate in hexanes (2 L) and ethyl acetate (3 L)). W369 was obtained as viscous syrup. $^1$H NMR (300 MHz, DMSO-$d_6$): δ 7.30-6.87 (m, 13H, C$\underline{H}$ on DMT), 4.62 (t, J=6.0 Hz, 1H, O$\underline{H}$), 4.04 (m, 4H, Fc-$\underline{H}$), 3.95 (m, 2H, C$\underline{H}_2$—O), 3.73 (s, 6H, C$\underline{H}_3$—O on DMT), 3.30 (m, 2H, C$\underline{H}_2$—OH), 2.88 (m, 4H, C$\underline{H}_2$—O, C$\underline{H}_2$CN), 2.30 (t, J=6.0 Hz, 2H, C$\underline{H}_2$-Fc), 1.78 (m, 2H, C$\underline{H}_2$—CH$_2$-Fc), 1.76 (s, 15H, Cp-C$\underline{H}_3$), 0.87 (s, 3H, C$\underline{H}_3$—C); $^{31}$P NMR (121.5 MHz, DMSO-$d_6$): −0.25 (s); MS positive mode: calcd. for ($C_{47}H_{58}FeNO_8P$) 851, found 851 (M$^+$), 872 (MNa$^+$).

Details of Synthesis of W370

To a solution of W369 (10.00 g, 11.8 mmol) in 100 mL anhydrous dichloromethane was added N,N-diisopropylethylamine (6.0 mL, 34.2 mmol) and the mixture was cooled to 0° C. After addition of N,N-Diisopropylethylamino cyanoethyl phosphoramidic chloride (3.6 mL, 16.1. mmol) at 0° C., the mixture was stirred at room temperature for 60 to 70 minutes. The organic layer was extracted by water, dried over anhydrous sodium sulfate and concentrated. It was observed that the product did not dissolve well in 10% EtOAc in hexane. After a fast column chromatography (silica gel: 150 g, packed with 0.5% DIPEA and 10% EtOAc in hexane; eluting solvents: 20% ethyl acetate in hexane (0.75 L); 30% ethyl acetate in hexane (2.0 L), then 50% ethyl acetate in hexanes (2.5 L), W370 was recovered as viscous syrup. It was dissolved in anhydrous acetonitrile (10 ml/g), and was filtered through a 0.45 u disk or 0.22 u filter paper. The solution was concentrated until no observable vapor development was seen. It was further co-evaporated twice with anhydrous acetonitrile, and was kept under high vacuum for at least 12 h. W370 was obtained as viscous liquid. $^1$H NMR (300 MHz, DMSO-$d_6$): δ 7.30-6.85 (m, 13H, C$\underline{H}$ on DMT), 4.07 (m, 4H, Fc-$\underline{H}$), 3.95 (m, 2H, C$\underline{H}_2$—O), 3.73 (s, 6H, C$\underline{H}_3$—O on DMT), 3.68 (m, 2H, (CH$_3$)$_2$—C$\underline{H}$—N), 3.62-3.48 (m, 4H, C$\underline{H}_2$—O), 2.95 (br, 2H, C$\underline{H}_2$—O), 2.86 (br, 2H, C$\underline{H}_2$—CN), 2.69 (t, J=6.0 Hz, 2H, C$\underline{H}_2$—CN), 2.30 (br, 2H, C$\underline{H}_2$-Fc), 1.80 (s, 15H, Cp-C$\underline{H}_3$), 1.78 (m, 2H, C$\underline{H}_2$—CH$_2$-Fc), 1.08-1.02 (m, 12H, (C$\underline{H}_3$)$_2$—CH—N), 0.94 (d, 3H, C$\underline{H}_3$—C). $^{31}$P NMR (121.5 MHz, DMSO-$d_6$) δ: 148.1 (s), 148.0 (s), −0.43 (s); $^{31}$P NMR major single peak (−0.5 ppm) integral ratio in the range of −10 to 20 ppm: >85%. MS positive mode: cald for ($C_{56}H_{75}FeN_3O_9P_2$) 1051, found 1052 (MH$^+$).

Example 2

Synthesis of Non-Nucleotide Ferrocene Label N330 and Intermediates

N330 has been developed as a Non-Nucleotide Ferrocene Label (NNFL) with a redox potential at ~160 mV vs. a reference Ag/AgCl electrode. This label can be incorporated into oligonucleotides to make signal probes for OMD's eSensor® DNA detection system and other ECD systems and applications.

N330 Synthesis Overview

Synthesis of intermediate QW50 from the starting material 1,1,1-tris(hydroxymethyl)ethane is shown in Scheme 1. Synthesis of N330 from the starting material ferrocene is shown in Scheme 2.

Scheme 1
Synthesis of QW50

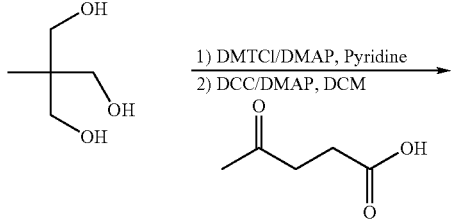

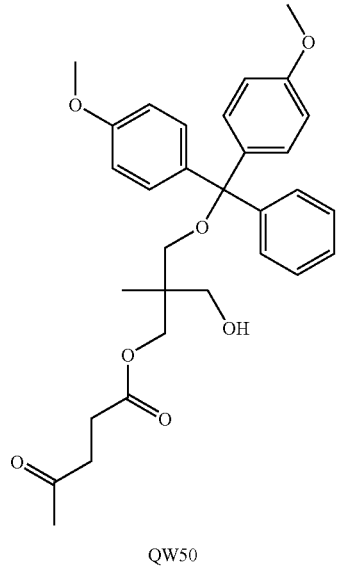

QW50

Scheme 2

Synthesis of N330 from Ferrocene

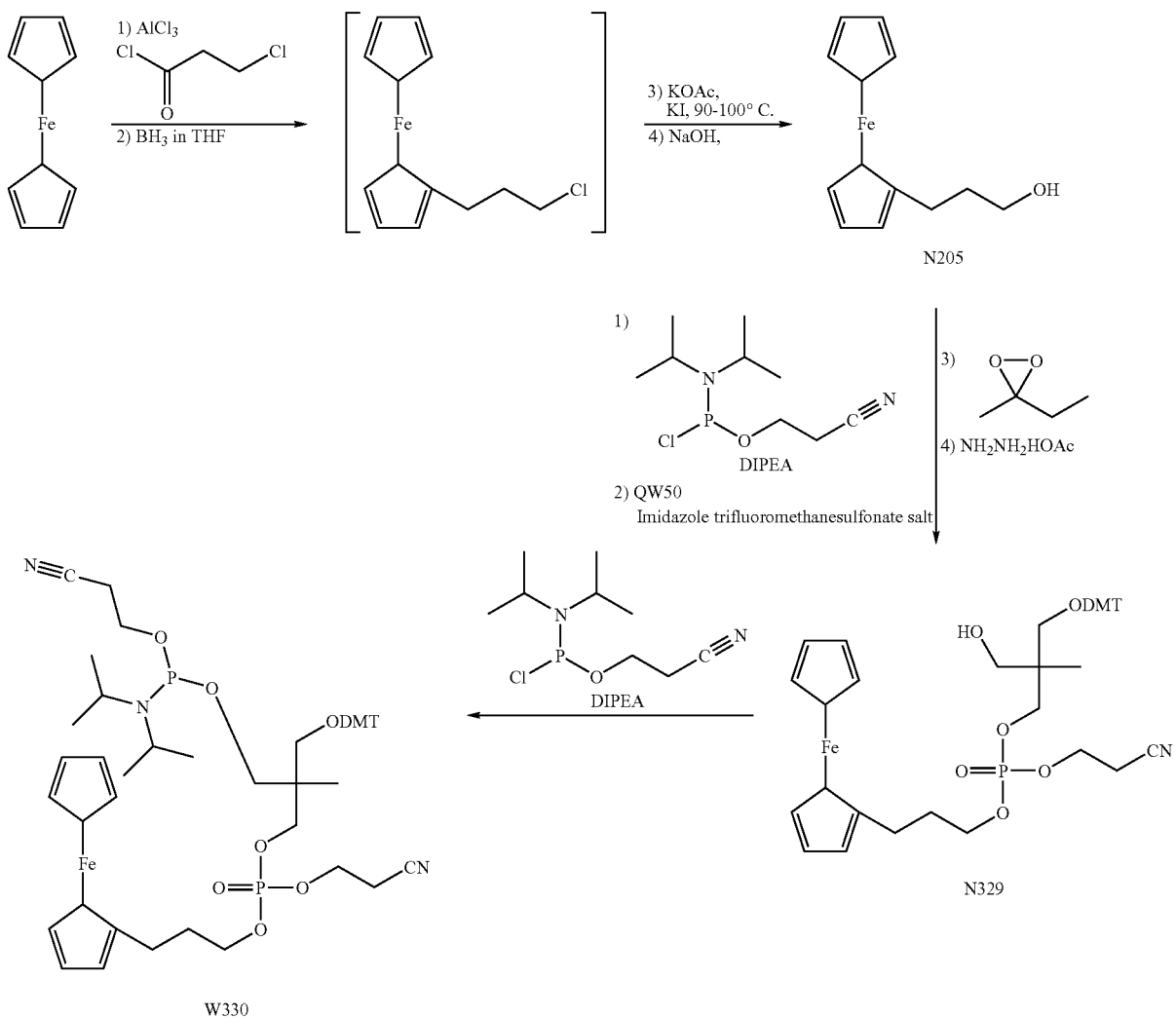

Details of Synthesis of Intermediate QW50

To a solution of 1,1,1-tris(hydroxymethyl)ethane (120.15 g, 1.00 mol) and 4-(dimethylamino)pyridine (0.12 g, 9.8 mmol) in 400 mL pyridine was added a solution of DMT-Cl (33.88 g 100 mmol) in 250 mL pyridine dropwise at room temperature. The mixture was stirred at room temperature for 60-70 min after the addition of DMT-Cl. After concentration, 300 mL of 5% sodium bicarbonate was added and the aqueous layer was extracted with three portions of 90% Ethyl acetate in hexanes. The combined organic layer was washed by water, dried with anhydrous sodium sulfate and the solvent was evaporated under reduced pressure. The residue was co-evaporated with toluene three times and dried on a vacuum line overnight. The residue was dissolved into 340 mL anhydrous dichloromethane and 1,3-dicyclohexylcarbodiimde (17.53 g, 84.75 mmol) was added. After cooling to 0° C., levulinic acid (9.87 g, 84.99 mmol) was added, followed by 4-(dimethylamino)pyridine (0.12 g, 9.8 mmol). The mixture was stirred at 0° C. for 120-150 min and 5 mL methanol was added, followed by addition of hexanes (340 mL). After filtration, the solution was concentrated. After purification by using column chromatography on silica gel (silica gel: 700 g; eluting solvents: 30% ethyl acetate in hexanes; 45% ethyl acetate in hexanes), QW50 was obtained as viscous syrup.

$^1$H-NMR (300 MHz, DMSO-$d_6$): δ 7.25 (m, 9H, C$\underline{H}$ on DMT), 6.85 (d, J=9.0 Hz, 4H, C$\underline{H}$ on DMT), 4.57 (t, J=5.1 Hz, 1H, O$\underline{H}$), 3.91 (m, 2H, C$\underline{H}_2$O), 3.71 (s, 6H, C$\underline{H}_3$O on DMT), 3.27 (m, 2H, C$\underline{H}_2$O), 2.83 (m, 2H, C$\underline{H}_2$O), 2.60 (t, J=6.6 Hz, 2H, C$\underline{H}_2$—CH$_2$), 2.32 (t, J=6.6 Hz, 2H, CH$_2$—C$\underline{H}_2$), 2.04 (s, 3H, C$\underline{H}_3$—CO), 0.82 (s, 3H, C$\underline{H}_3$—C). Anal. calcd. for (C$_{31}$H$_{36}$O$_7$Na): 543, found 543.

Details of Synthesis of Intermediate N205

To a solution of ferrocene (20.00 g, 107 mmol) in 150 mL anhydrous dichloromethane was added 3-chloropropionyl chloride (11.8 mL, 127 mmol) and the mixture was cooled to 0° C. After addition of aluminum chloride (16.48 g, 122 mmol) at 0° C., the mixture was stirred at room temperature for 60-90 minutes. The mixture was cooled to 0° C. and Borane in THF (134.4 mL of 1 M solution in THF, 134.4 mmol) was added. After stirring at room temperature for 40-45 minutes, the mixture was poured into ice/water and 350 mL hexanes were added. The organic layer was separated, washed by water, dried with anhydrous sodium sulfate and concentrated. The residue was dissolved in 200 mL of N,N-Dimethylformamide and potassium acetate (15.83 g, 161 mmol) was added, followed by potassium iodide (17.85 g, 108 mmol). The mixture was heated and stirred at 95+/−5° C. for 60-70 minutes. After cooling to room temperature, 134.3 mL of 4M NaOH solution was added and the mixture was stirred at room temperature for 45-60 minutes. 250 mL water was added and the mixture was extracted with three portions of 80% ethyl acetate in hexanes. The combined organic layer was washed by water, dried with anhydrous sodium sulfate and concentrated. After pad filtration on a column-funnel with 200 g Silica gel (eluting solvents: 5% ethyl acetate in hexanes and 30% ethyl acetate in hexanes), N205 was obtained as orange-colored viscous liquid. GC/MS: retention time: 11.76 minutes; purity: 100%; M/e: 244 (M+, 100), 199 (25), 121 (20). $^1$H-NMR (300 MHz, DMSO-$d_6$): δ 4.40 (t, J=5.4 Hz, 1H, OH), 4.10-4.01 (m, 9H, Fc-H), 3.41 (m, 2H, CH$_2$—OH), 2.30 (m, 2H, CH$_2$-Fc), 1.61 (m, 2H, CH$_2$).

Details of Synthesis of Intermediate N329

To a solution of N205 (9.77 g, 40.0 mmol) in 100 mL anhydrous dichloromethane was added N,N-diisopropylethylamine (9.1 mL, 51.8 mmol) and the mixture was cooled to 0° C. After addition of N,N-Diisopropylethylamino cyanoethyl phosphoramidic chloride (9.5 mL, 42.4 mmol) at 0° C., the mixture was stirred at room temperature for 60-70 minutes. QW50 (25.00 g, 48.0 mmol) in 125 mL anhydrous dichloromethane was added, followed by addition of imidazole trifluoromethanesulfonate salt (11.30 g, 52.0 mmol) in 40 mL acetonitrile. After stirring at room temperature for 60-70 minutes, the mixture was cooled to 0° C. and 2-butanone peroxide (11.8 mL of 3.6 M solution, 42.5 mmol) in 50 mL anhydrous dichloromethane was added. The reaction was stirred at 0° C. for 10 minutes. Hydrazine acetate (18.43 g, 200 mmol) in 125 mL methanol was added and the reaction was stirred at room temperature for 60-70 minutes. The organic layer was washed by water, 5% sodium bicarbonate, dried with anhydrous sodium sulfate and concentrated. After column chromatography on silica gel (silica gel: 400 g; eluting solvents: 10% ethyl acetate in hexanes; 50% ethyl acetate in hexanes; 75% ethyl acetate in hexanes and ethyl acetate), N329 was obtained as viscous syrup. $^1$H NMR (300 MHz, DMSO-$d_6$): δ 7.30-6.85 (m, 13H, CH on DMT), 4.64 (t, J=6.0 Hz, 1H, OH), 4.03 (m, 9H, Fc-H), 3.95 (m, 6H, CH$_2$—O), 3.71 (s, 6H, CH$_3$—O on DMT), 3.30 (m, 2H, CH$_2$—OH), 2.88 (m, 4H, CH$_2$—O, CH$_2$CN), 2.30 (t, J=6.0 Hz, 2H, CH$_2$-Fc), 1.78 (m, 2H, CH$_2$—CH$_2$-Fc), 0.87 (s, 3H, CH$_3$—C); $^{31}$P NMR (121.5 MHz, DMSO-$d_6$): −0.31 (s); MS positive mode: calcd. for ($C_{42}H_{48}FeNO_8P$) 781, found 804 (MNa+).

Details of Synthesis of N330

To a solution of N329 (16.30 g, 20.87 mmol) in 166 mL anhydrous dichloromethane was added N,N-diisopropylethylamine (6.80 mL, 38.71 mmol) and the mixture was cooled to ° C. After addition of N,N-Diisopropylethylamino cyanoethyl phosphoramidic chloride (6.20 mL, 27.67 mmol) at 0° C., the mixture was stirred at room temperature for 60-70 minutes. The organic layer was washed with water, dried with anhydrous sodium sulfate and concentrated. After column chromatography (silica gel: 150 g; eluting solvents: 30% ethyl acetate in hexanes; 50% ethyl acetate in hexanes), N330 was obtained as viscous syrup. $^1$H NMR (300 MHz, DMSO-$d_6$): δ 7.30-6.85 (m, 13H, CH on DMT), 4.03 (m, 9H, Fc-H), 3.95 (m, 6H, CH$_2$—O), 3.71 (s, 6H, CH$_3$—O on DMT), 3.69 (m, 2H, (CH$_3$)$_2$—CH—N), 3.62-3.48 (m, 4H, CH$_2$—O), 2.94 (br, 2H, CH$_2$—O), 2.86 (br, 2H, CH$_2$—CN), 2.68 (t, J=6.0 Hz, 2H, CH$_2$—CN), 2.30 (br, 2H, CH$_2$-Fc), 1.78 (m, 2H, CH$_2$—CH$_2$-Fc), 1.08-1.02 (m, 12H, (CH$_3$)$_2$—CH—N), 0.95 (s, s, 3H, CH$_3$—C). $^{31}$P NMR (121.5 MHz, DMSO-$d_6$) δ: 147.7 (s), 147.6 (s), −0.5 (s); $^{31}$P NMR major single peak (−0.5 ppm) integral in the range of −10 to 20 ppm: 100%. MS positive mode: cald for ($C_{51}H_{65}FeN_3O_9P_2$) 981, found 981 (M+), 1005 (MNa+).

Synthesis of Signal Probe D6002 Using N330

The signal probes were synthesized by the Biopolymer Group using ABI 392/394 RNA/DNA synthesizers with CMS proprietary procedures. Four units of N330 were incorporated into a DNA consecutively. The crude signal probes were purified on a Hitachi 7200 semi-preparative HPLC, using a CMS method "R3-0%45%100% fc25-35". The concentrations of the DNA stocks were measured by UV absorbance. Three batches of a signal probe (D6002) were synthesized from 3 different batches of N330. These signal probes were analyzed by Capillary Electrophoresis (CE) per SOP EQ037.04 and MALDI-TOF by HT Labs in San Diego.

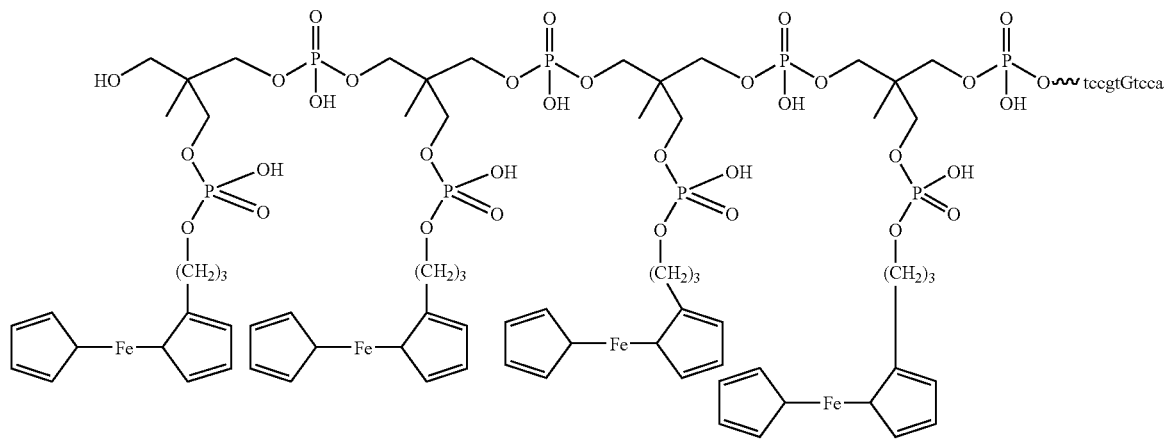

Structure of signal probe D6002: (N330)(N330)(N330)(N330)-tccgtGtccac [SEQ ID No:1]

Example 3

Synthesis of Non-Nucleotide Ferrocene Label QW56 and Intermediates

QW56 has been developed as a Non-Nucleotide Ferrocene Label (NNFL) with a redox potential at ~320 mV vs. a reference Ag/AgCl electrode. This label can be incorporated into oligonucleotides to make signal probes for OMD's eSensor® DNA detection system and other ECD systems and applications.

Synthesis Overview

Synthesis of QW56 from the Starting Material Ferrocene is Shown in Scheme 1.

Details of Synthesis of Intermediate CT192

A solution of ferrocene (60.00 g, 322.5 mmol) in dry THF (370 mL) and dry hexane (370 mL) was cooled to −10 to −5° C. in an acetone/dry ice bath. Under efficient stirring, t-Butyllithium (228.0 mL of 1.5 M solution in pentane, 342.0 mmole) was added to the reaction flask dropwise via an additional funnel under argon pressure over a period of 45 to 60 minutes, during which the temperature was controlled at −5 to 0° C. by replenishing the dry ice. After stirred for additional 10 to 15 minutes at −5 to 0° C., 370 mL of dry hexane was added and the mixture was cooled to −78 to −50° C. to precipitate the crude product. The precipitate was filtered by Schlenk filtration and washed with approximately 5 to 8 portions of 120 mL of hexane until the filtrate was almost colorless. The reaction flask containing the yellow solid of the lithioferrocene was cooled to −78° C. under argon atmosphere and 1000 mL dry THF was introduced to the reaction

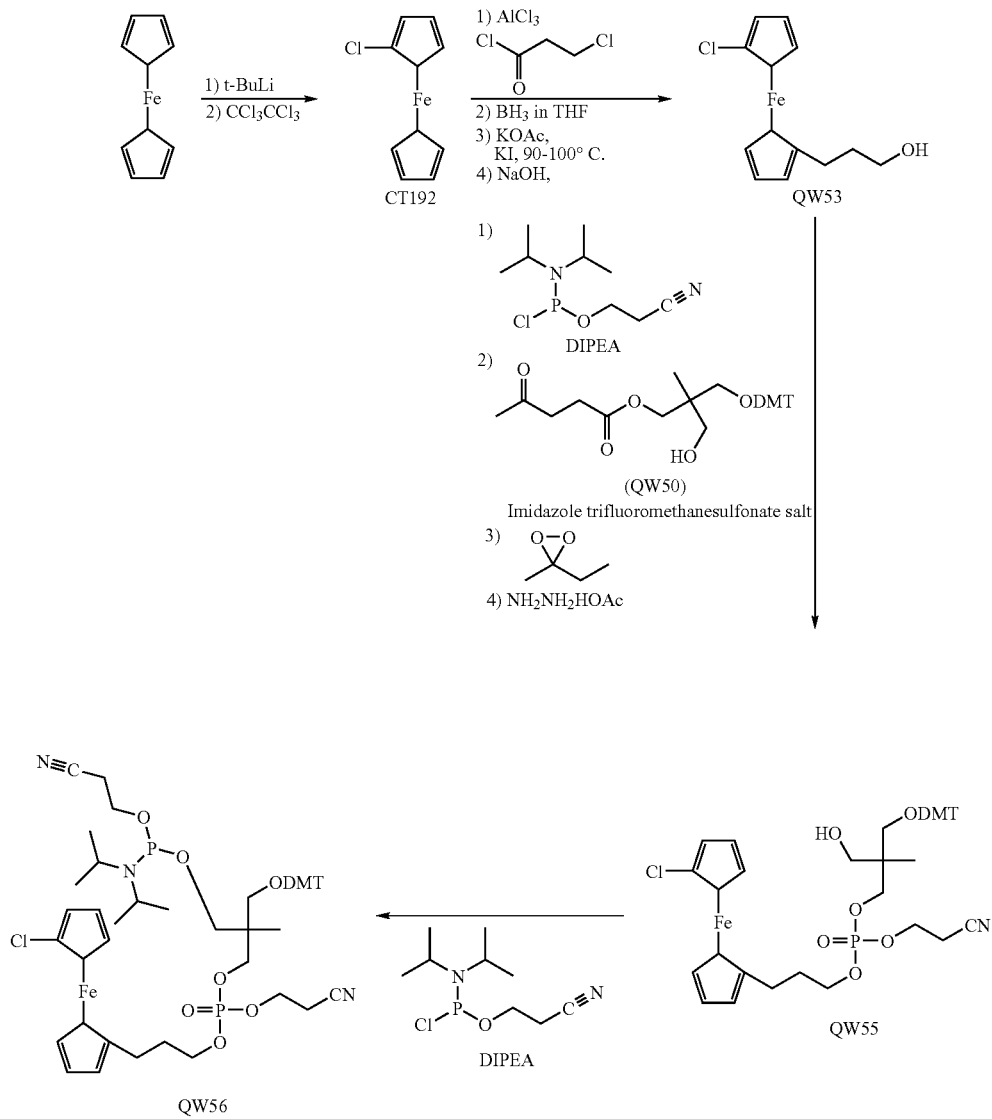

Scheme 1 flask. Hexachloro-ethane (60.00 g, 253.5 mmol) was added and the mixture was stirred at −78° C. for 30-45 minutes. After warming up to room temperature, the solvent was removed under reduced pressure. 500 mL DCM (dichloromethane) was added to dissolve the residue and 2-butonoe peroxide (22.4 mL of 3.6 M solution) was added to the mixture dropwise over 15-30 minute to oxidize the remaining ferrocene. After stirring at room temperature for 30-40 minutes, the mixture was filtered through a pad of Celite 545 (100 g) and the filtrate was subsequently quenched with a sodium thiosulfate solution (50 g sodium thiosulfate pentahydrate in 250 mL water) by stirring mixture for 10 to 20 hours. The organic layer was separated and washed by water (2×200 mL), dried over $Na_2SO_4$, and concentrated. After concentration, the crude product was purified by pad filtration on 800 g silica gel (eluting solvent: hexane) to yield CT192 as orange-colored solid. GC/MS: retention time: 8.8 min. m/e 220 (100, M), 184 (60), 128 (50), 56 (30). $^1$H-NMR (300 MHz, DMSO-$d_6$): δ 4.45 (t, J=2.1 Hz, 2H, CH on Cl-substituted cyclopentadiene ring), 4.25 (s, 5H, CH on cyclopentadiene ring), 4.14 (t, J=2.1 Hz, 2H, CH on Cl-substituted cyclopentadiene ring).

Details of Synthesis of Intermediate QW53

To a solution of CT192 (20.00 g, 90.71 mmol) in 150 mL anhydrous dichloromethane was added 3-chloropropionyl chloride (8.8 mL, 94.7 mmol) and the mixture was cooled to 0° C. After addition of aluminum chloride (13.40 g, 99.20 mmol) at 0° C., the mixture was stirred at room temperature for 60-90 minutes. The mixture was cooled to 0° C. and Borane in THF (110.0 mL of 1 M solution in THF, 110.0 mmol) was added. After stirring at room temperature for 40-45 minutes, the mixture was poured into ice/water and 350 mL hexanes were added. The organic layer was separated, washed by water, dried with anhydrous sodium sulfate and concentrated. The residue was dissolved in 200 mL of N,N-Dimethylformamide and potassium acetate (10.70 g, 108.8 mmol) was added, followed by potassium iodide (10.70 g, 64.7 mmol). The mixture was heated and stirred at 95+/−5° C. for 60-70 minutes. After cooling to room temperature, 113.5 mL of 4M NaOH solution was added and the mixture was stirred at room temperature for 45-60 minutes. 250 mL water was added and the mixture was extracted with three portions of 80% ethyl acetate in hexanes. The combined organic layer was washed by water, dried with anhydrous sodium sulfate and concentrated. After pad filtration on a column-funnel with 200 g Silica gel (eluting solvents: 5% ethyl acetate in hexanes and 30% ethyl acetate in hexanes), QW53 was obtained as orange-colored viscous liquid. GC/MS: retention time: 12.77 minutes; purity: 100%; M/e: 278 (M$^+$, 100). $^1$H-NMR (300 MHz, DMSO-$d_6$): δ 4.43-4.39 (m, 1H, O$\underline{H}$), 4.18-4.09 (m, 8H, Fc-$\underline{H}$), 3.41 (m, 2H, C$\underline{H}_2$—OH), 2.33 (m, 2H, C$\underline{H}_2$-Fc), 1.61 (m, 2H, C$\underline{H}_2$).

Details of Synthesis of Intermediate QW55

To a solution of QW53 (11.15 g, 40.0 mmol) in 100 mL anhydrous dichloromethane was added N,N-diisopropylethylamine (9.1 mL, 51.8 mmol) and the mixture was cooled to 0° C. After addition of N,N-Diisopropylethylamino cyanoethyl phosphoramidic chloride (9.5 mL, 42.4 mmol) at 0° C., the mixture was stirred at room temperature for 60-70 minutes. QW50 (25.00 g, 48.0 mmol) in 125 mL anhydrous dichloromethane was added, followed by addition of imidazole trifluoromethanesulfonate salt (11.30 g, 52.0 mmol) in 40 mL acetonitrile. After stirring at room temperature for 60-70 minutes, the mixture was cooled to 0° C. and 2-butanone peroxide (11.8 mL of 3.6 M solution, 42.5 mmol) in 50 mL anhydrous dichloromethane was added. The reaction was stirred at 0° C. for 10 minutes. Hydrazine acetate (18.43 g, 200 mmol) in 125 mL methanol was added and the reaction was stirred at room temperature for 60-70 minutes. The organic layer was washed by water, 5% sodium bicarbonate, dried with anhydrous sodium sulfate and concentrated. After column chromatography on silica gel (silica gel: 400 g; eluting solvents: 10% ethyl acetate in hexanes; 50% ethyl acetate in hexanes; 75% ethyl acetate in hexanes and ethyl acetate), QW55 was obtained as viscous syrup. $^1$H NMR (300 MHz, DMSO-$d_6$): δ 7.30-6.85 (m, 13H, C$\underline{H}$ on DMT), 4.64 (t, J=6.0 Hz, 1H, O$\underline{H}$), 4.36-4.03 (m, 8H, Fc-$\underline{H}$), 3.95 (m, 6H, C$\underline{H}_2$—O), 3.71 (s, 6H, C$\underline{H}_3$—O on DMT), 3.30 (m, 2H, C$\underline{H}_2$—OH), 2.88 (m, 4H, C$\underline{H}_2$—O, C$\underline{H}_2$CN), 2.30 (t, J=6.0 Hz, 2H, C$\underline{H}_2$-Fc), 1.78 (m, 2H, C$\underline{H}_2$—CH$_2$-Fc), 0.87 (s, 3H, C$\underline{H}_3$—C); $^{31}$P NMR (121.5 MHz, DMSO-$d_6$): −0.31 (s); MS positive mode: calcd. for ($C_{42}H_{47}ClFeNO_8P$) 815, found 815 (M$^+$), 838 (MNa$^+$).

Details of Synthesis of QW56

To a solution of QW55 (17.00 g, 20.83 mmol) in 170 mL anhydrous dichloromethane was added N,N-diisopropylethylamine (6.70 mL, 38.14 mmol) and the mixture was cooled to ° C. After addition of N,N-Diisopropylethylamino cyanoethyl phosphoramidic chloride (6.30 mL, 28.11 mmol) at 0° C., the mixture was stirred at room temperature for 60-70 minutes. The organic layer was washed with water, dried with anhydrous sodium sulfate and concentrated. After column chromatography (silica gel: 150 g; eluting solvents: 30% ethyl acetate in hexanes; 50% ethyl acetate in hexanes), QW56 was obtained as viscous syrup. $^1$H NMR (300 MHz, DMSO-$d_6$): δ 7.30-6.85 (m, 13H, C$\underline{H}$ on DMT), 4.36-4.04 (m, 8H, Fc-$\underline{H}$), 3.95 (m, 6H, C$\underline{H}_2$—O), 3.71 (s, 6H, C$\underline{H}_3$—O on DMT), 3.69 (m, 2H, (CH$_3$)$_2$—C$\underline{H}$—N), 3.48 (m, 4H, C$\underline{H}_2$—O), 2.94 (br, 2H, C$\underline{H}_2$—O), 2.86 (br, 2H, C$\underline{H}_2$—CN), 2.68 (t, J=6.0 Hz, 2H, C$\underline{H}_2$—CN), 2.33 (br, 2H, C$\underline{H}_2$-Fc), 1.78 (m, 2H, C$\underline{H}_2$—CH$_2$-Fc), 1.08-1.02 (m, 12H, (C$\underline{H}_3$)$_2$—CH—N), 0.95 (s, s, 3H, C$\underline{H}_3$—C). $^{31}$P NMR (121.5 MHz, DMSO-$d_6$) δ: 147.8 (s), 147.7 (s), −0.46 (s); $^{31}$P NMR major single peak (−0.5 ppm) integral in the range of −10 to 20 ppm: 100%. MS positive mode: cald for ($C_{51}H_{64}ClFeN_3O_9P_2$) 1016, found 1016 (M$^+$), 1038 (MNa$^+$).

Synthesis of a Signal Probe D5994 Using QW56

The signal probes were synthesized by the BioSystems Group using ABI 392/394 RNA/DNA synthesizers with CMS proprietary procedures. Four units of QW56 were incorporated into a DNA consecutively. The crude signal probes were purified on a Hitachi 7200 semi-preparative HPLC, using a CMS method "R3-0%45%100% fc27-37". The description of HPLC method is attached in Appendix 8. The concentrations of the DNA stocks were measured by UV absorbance. Three batches of a signal probe (D5994) were synthesized from 3 different batches of QW56. These signal probes were analyzed by Capillary Electrophoresis (CE) per SOP EQ037.04 and MALDI-TOF by HT Labs in San Diego.

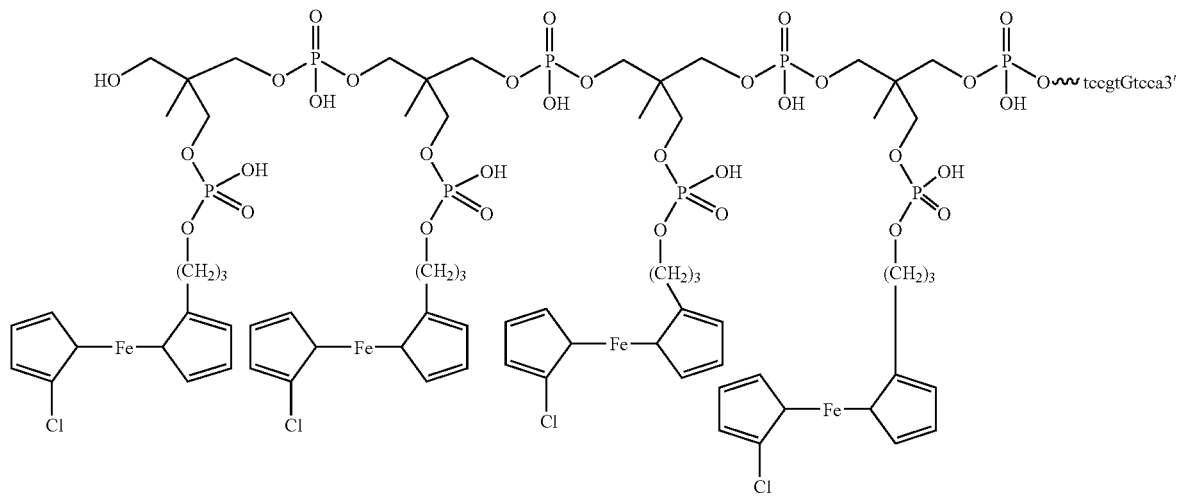

Structure of signal probe D5994: (QW56)(QW56)(QW56)(QW56)-tccgtGtccac [SEQ ID NO:2]

Example 4

Synthesis of Non-Nucleotide Ferrocene Label QW80 and Intermediates

QW80 has been developed as a Non-Nucleotide Ferrocene Label (NNFL) with a redox potential at ~480 mV vs. reference Ag/AgCl electrode. This label can be incorporated into oligonucleotides to make signal probes for OMD's eSensor® DNA detection system and other ECD systems and applications.

QW80 Synthesis Overview

Synthesis of QW80 from the starting material ferrocene is shown in Scheme 1.

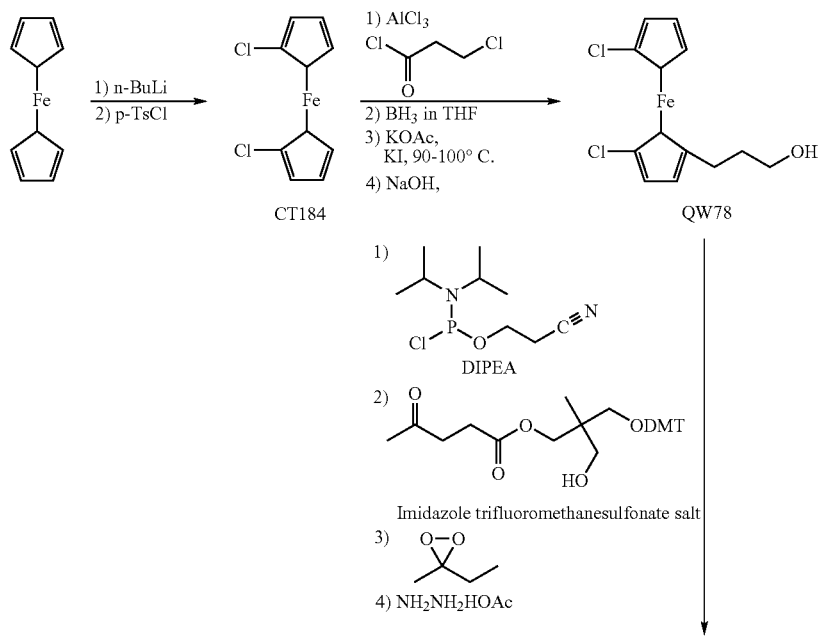

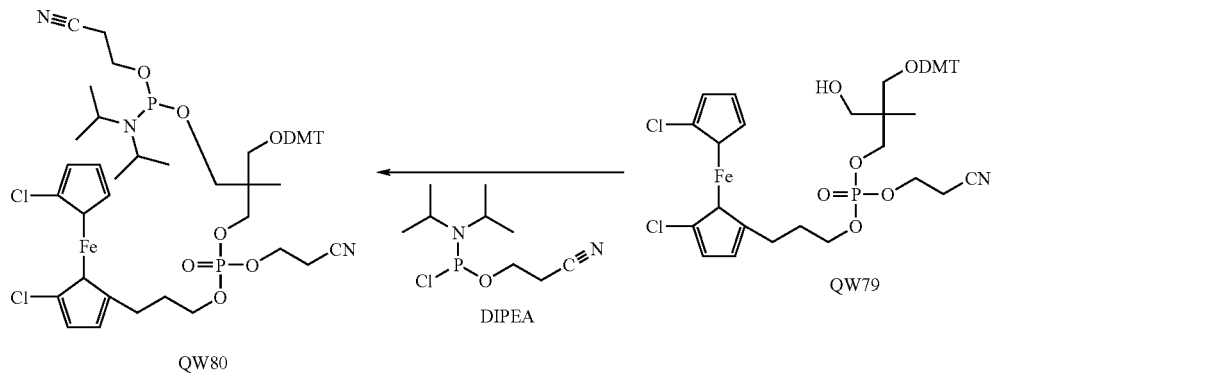

QW80    DIPEA    QW79

Details of Synthesis of Intermediate CT184

To a solution of ferrocene (30.00 g, 161.2 mmol) in 500 mL dry diethyl ether was added TMEDA (27 mL, 178.9 mmol) at room temperature, followed by addition of n-Butyllithium (300 mL of 1.6 M solution in hexanes, 480.0 mmole). After stirring at room temperature for 15-24 hours, the mixture was cooled to −78° C. and toluenesulfonyl chloride (91.50 g, 480.0 mmol) was added. After stirring at −78° C. for 1 hour, the reaction mixture was warmed up to room temperature and 75 mL of water was added. 450 mL of Hexanes was added and the mixture was washed by water (3×400 mL), dried with anhydrous sodium sulfate and concentrated. The crude product was purified by pad filtration on 500 g silica gel (eluting solvents: hexanes). The orange-colored band was collected and the solvents were removed. The product was recrystallized by hexanes to yield CT184 as yellow solid. GC/MS: retention time: 9.9 min. m/e 254 (72, M), 128 (100), $^1$H-NMR (300 M Hz, DMSO-$d_6$): δ4.55 (t, J=1.9 Hz, 4H, C$\underline{H}$ next to CCl), 4.25 (t, J=1.9 Hz, 4H, C$\underline{H}$).

Details of Synthesis of Intermediate QW78

To a solution of CT184 (20.00 g, 78.46 mmol) in 150 mL anhydrous dichloromethane was added 3-chloropropionyl chloride (8.3 mL, 89.3 mmol) and the mixture was cooled to 0° C. After addition of aluminum chloride (12.55 g, 92.90 mmol) at 0° C., the mixture was stirred at room temperature for 60-90 minutes. The mixture was cooled to 0° C. and Borane in THF (140.0 mL of 1 M solution in THF, 140.0 mmol) was added. After stirring at room temperature for for 15-24 hours, the mixture was poured into ice/water and 350 mL hexanes were added. The organic layer was separated, washed by water, dried with anhydrous sodium sulfate and concentrated. The residue was dissolved in 200 mL of N,N-Dimethylformamide and potassium acetate (9.25 g, 94.1 mmol) was added, followed by potassium iodide (9.25 g, 55.9 mmol). The mixture was heated and stirred at 95+/−5° C. for 60-70 minutes. After cooling to room temperature, 100 mL of 4M NaOH solution was added and the mixture was stirred at room temperature for 45-60 minutes. 250 mL water was added and the mixture was extracted with three portions of 80% ethyl acetate in hexanes. The combined organic layer was washed by water, dried with anhydrous sodium sulfate and concentrated. After pad filtration on a column-funnel with 250 g Silica gel (eluting solvents: 5% ethyl acetate in hexanes; 15% ethyl acetate in hexanes; 30% ethyl acetate in hexanes), QW78 was obtained as orange-colored viscous liquid. GC/MS: retention time: GC/MS: retention time: 13.53, 13.60; purity: 100%; M/e: 312 (M$^+$, 100). $^1$H-NMR (30 0̸ M Hz, DMSO-$d_6$): δ4.48 (m, 1H, O$\underline{H}$), 4.44-4.43 (m, 7H, Fc-$\underline{H}$), 3.41 (m, 2H, C$\underline{H}_2$—OH), 2.45-2.25 (m, m, 2H, C$\underline{H}_2$-Fc), 1.61 (m, 2H, C$\underline{H}_2$).

Details of Synthesis of Intermediate QW79

To a solution of QW78 (12.50 g, 40.0 mmol) in 100 mL anhydrous dichloromethane was added N,N-diisopropylethylamine (9.1 mL, 51.8 mmol) and the mixture was cooled to 0° C. After addition of N,N-Diisopropylethylamino cyanoethyl phosphoramidic chloride (9.5 mL, 42.4 mmol) at 0° C., the mixture was stirred at room temperature for 60-70 minutes. QW50 (25.00 g, 48.0 mmol) in 125 mL anhydrous dichloromethane was added, followed by addition of imidazole trifluoromethanesulfonate salt (11.30 g, 52.0 mmol) in 40 mL acetonitrile. After stirring at room temperature for 60-70 minutes, the mixture was cooled to 0° C. and 2-butanone peroxide (11.8 mL of 3.6 M solution, 42.5 mmol) in 50 mL anhydrous dichloromethane was added. The reaction was stirred at 0° C. for 10 minutes. Hydrazine acetate (18.43 g, 200 mmol) in 125 mL methanol was added and the reaction was stirred at room temperature for 60-70 minutes. The organic layer was washed by water, 5% sodium bicarbonate, dried with anhydrous sodium sulfate and concentrated. After column chromatography on silica gel (silica gel: 400 g; eluting solvents: 10% ethyl acetate in hexanes; 50% ethyl acetate in hexanes; 75% ethyl acetate in hexanes and ethyl acetate), QW79 was obtained as viscous syrup. $^1$H NMR (300 MHz, DMSO-$d_6$): δ 7.30-6.85 (m, 13H, C$\underline{H}$ on DMT), 4.64 (m, 1H, O$\underline{H}$), 4.42-4.07 (m, 7H, Fc-$\underline{H}$), 3.95 (m, 6H, C$\underline{H}_2$—O), 3.71 (s, 6H, C$\underline{H}_3$—O on DMT), 3.30 (m, 2H, C$\underline{H}_2$—OH), 2.88 (m, 4H, C$\underline{H}_2$—O, C$\underline{H}_2$CN), 2.48-2.25 (m, 2H, C$\underline{H}_2$-Fc), 1.78 (m, 2H, C$\underline{H}_2$—CH$_2$-Fc), 0.87 (s, 3H, C$\underline{H}_3$—C); $^{31}$P NMR (121.5 MHz, DMSO-$d_6$): −0.34 (s); MS positive mode: calcd. for ($C_{42}H_{46}Cl_2FeNO_8P$) 849, found 872 (MNa$^+$).

Details of Synthesis of Intermediate QW80

To a solution of QW79 (18.00 g, 21.16 mmol) in 180 mL anhydrous dichloromethane was added N,N-diisopropylethylamine (6.70 mL, 38.14 mmol) and the mixture was cooled to ° C. After addition of N,N-Diisopropylethylamino cyanoethyl phosphoramidic chloride (6.30 mL, 28.11 mmol) at 0° C., the mixture was stirred at room temperature for 60-70 minutes. The organic layer was washed with water, dried with anhydrous sodium sulfate and concentrated. After column chromatography (silica gel: 200 g; eluting solvents: 30% ethyl acetate in hexanes; 50% ethyl acetate in hexanes), QW80 was obtained as viscous syrup. $^1$H NMR (300 MHz, DMSO-$d_6$): δ 7.38-6.85 (m, 13H, C$\underline{H}$ on DMT), 4.42-4.08 (m, 7H, Fc-$\underline{H}$), 4.06-3.90 (m, 6H, C$\underline{H}_2$—O), 3.71 (s, 6H, C$\underline{H}_3$—O on DMT), 3.69 (m, 2H, (CH$_3$)$_2$—C$\underline{H}$—N), 3.48 (m, 4H, C$\underline{H}_2$—O), 2.94 (br, 2H, C$\underline{H}_2$—O), 2.87 (br, 2H, C$\underline{H}_2$—CN), 2.68 (t, J=6.0 Hz, 2H, C$\underline{H}_2$—CN), 2.45-2.25 (m, 2H, C$\underline{H}_2$-Fc, 2 isomers), 1.80 (m, 2H, C$\underline{H}_2$—CH$_2$-Fc), 1.11-1.02 (m, 12H, (C$\underline{H}_3$)$_2$—CH—N), 0.95 (s, s, 3H, C$\underline{H}_3$—C). $^{31}$P NMR (121.5 MHz, DMSO-$d_6$) δ: 147.8 (s), 147.7 (s), −0.47 (s); $^{31}$P NMR major single peak (−0.5 ppm) integral in the range of −10 to 20 ppm: 98%. MS positive mode: cald for (C$_{51}$H$_{63}$Cl$_2$FeN$_3$O$_9$P$_2$) 1049, found 1072 (MNa$^+$).

Synthesis of Signal Probe D6036 Using QW80

The signal probes were synthesized by the BioSystems Group using ABI 392/394 RNA/DNA synthesizers with CMS proprietary procedures. Four units of QW80 were incorporated into a DNA consecutively. The crude signal probes were purified on a Hitachi 7200 semi-preparative HPLC, using a CMS method "R3-0%45%100% fc27-37". The description of HPLC method is attached in Appendix 7. The concentrations of the DNA stocks were measured by UV absorbance. Three batches of a signal probe (D6036) were synthesized from 3 different batches of QW80. These signal probes were analyzed by Capillary Electrophoresis (CE) per SOP EQ037.04 and MALDI-TOF by HT Labs in San Diego.

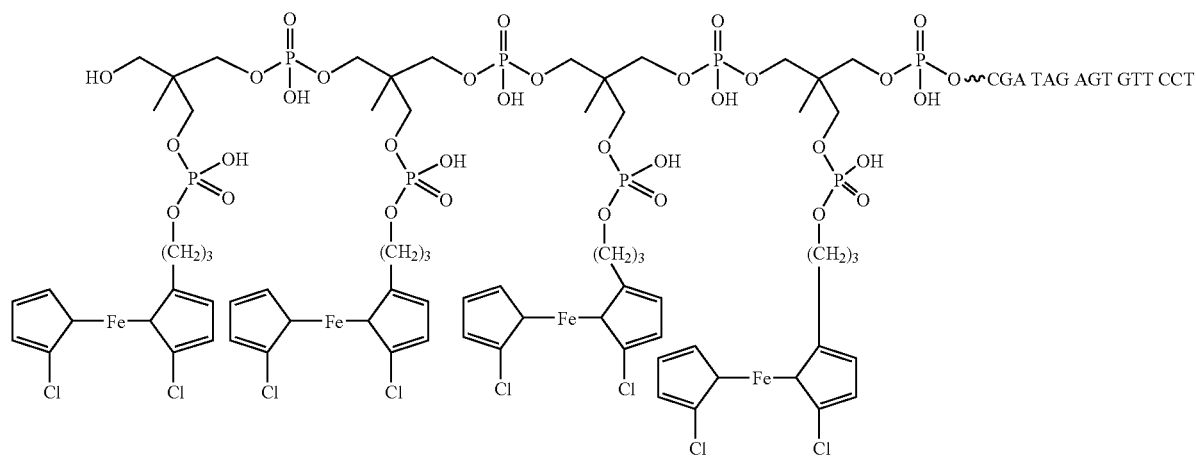

D6036: (QW80)(QW80)(QW80)(QW80)-CGA TAG AGT GTT CCT [SEQ ID NO:3]

Example 5

Synthesis of Reverse Linker Phosphoramidite W330 and Intermediate

W330 is a phosphoramidite linker with thiol acetic ester functionality. It can be incorporated into oligonucleotides at the 5'end, and allows the construction of reverse Capture Probes (CPs) for use in OMD's eSensor® DNA detection system and other ECD systems and applications.

Synthesis Overview

Synthesis of W330 from the Precursor 16-Bromohexadecarboxylic Acid

Scheme 1

Synthesis of W330

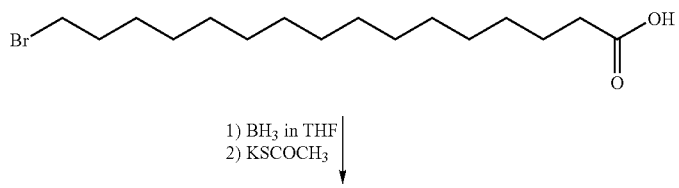

-continued

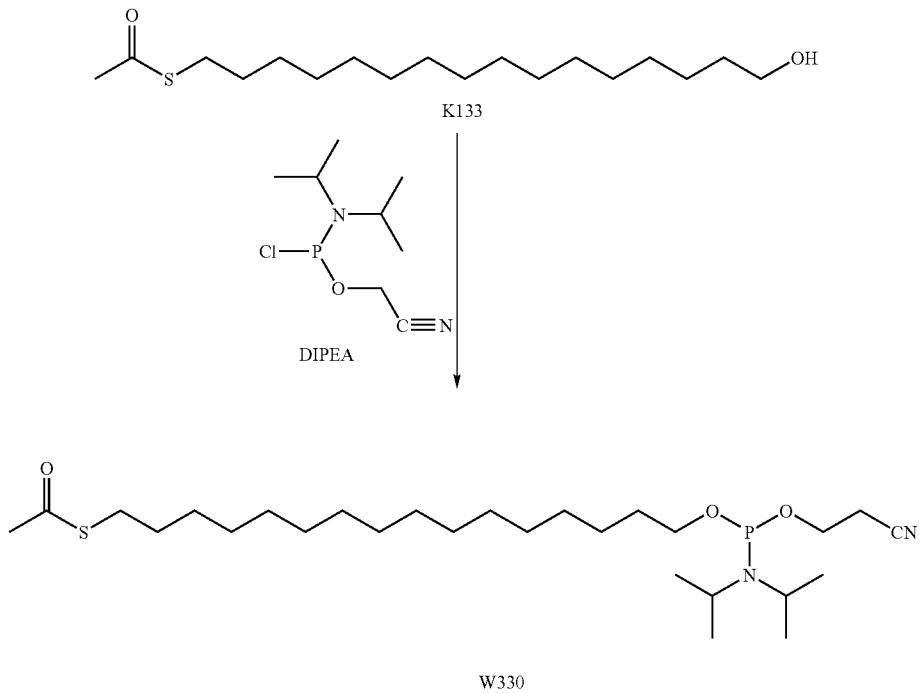

Details of Synthesis of Intermediate K133

To a solution of 16-bromohexadecarboxylic acid (10.00 g, 30.0 mmol) in 80 ml THF was added $BH_3$ (70 ml, 70 mmol, 1 M in THF) slowly at 0° C. After addition, the reaction mixture was stirred at room temperature for 60-90 minute. The mixture was cooled to 0° C. and 80 mL water was added. The aqueous layer was extracted with hexanes (2×100 mL). The combined organic layer was washed by 100 mL water, dried with sodium sulfate and concentrated to give a white solid. The solid was dissolved into). To a solution of this while solid in 100 mL DMF was added potassium thioacetate at room temperature. After stirring at room temperature for 60-90 minutes, 150 mL ethyl acetate was added to the reaction mixture, followed by 450 mL hexanes and 50 mL water. After being washed by three portions of water, the organic layer was dried over sodium sulfate and concentrated. After column chromatography on silica gel (silica gel: (200 g; eluting solvents: 5% ethyl acetate in hexanes; 15% ethyl acetate in hexanes; 25% ethyl acetate in hexanes), K133 was obtained as a white solid. $^1$H NMR (300 MHz, DMSO-$d_6$) δ 4.31 (t, J=5.1 Hz, 1H, OH), 3.37 (t, J=5.1 Hz, 2H, $CH_2OH$), 2.81 (t, J=6.9 Hz, 2H, $SCH_2$), 2.31 (s, 3H, $CH_3COS$), 1.50 (m, 2H, $CH_2CH2OH$), 1.40 (m, 2H, $CH_2CH2S$), 1.23 (br s, 24H, $CH_2$).

Details of Synthesis of W330

To a solution of K133 (8.00 g, 25.3 mmol) in 160 ml dichloromethane was added diisopropylethylamine (DIPEA) (22 mL, 125.2 mmol), followed by N,N-Diisopropylethylamino cyanoethyl phosphoramidic chloride (6.20 mL, 27.67 mmol) at 0° C. After stirring at to room temperature for 60-70 minutes, the mixture was washed by water (2×80 mL), dried over sodium sulfate and concentrated. The crude product was purified on a column of 160 g silica gel (eluting solvents: 1% TEA in 2.5% EtOAc/97.5% Hexane; 1% TEA in 5% EtOAc/95% Hexane; 1% TEA in 10% EtOAc/90% Hexane) to produce W330 as a clear liquid. $^1$H NMR (300 MHz, DMSO-$d_6$): δ 3.70 (m, 2H, —PNCH), 3.55 (m, 4H, $POCH_2CH_2CH_2$ and $POCH_2CH_2CN$), 2.82 (m, 4H, $SCH_2$, $CH_2CN$), 2.29 (s, 3H, $CH_3COS$) 1.50 (m, 4H, $CH_3COCH_2CH_2(CH_2)_{12}(CH_2)$ $(CH_2)OP$), 1.36-1.24 (m, 24H, $CH_3COCH_2CH_2(CH_2)_{12}$ $(CH_2)$—$(CH_2)OP$)), 1.19-1.16 (m, 12H, $N(CH(CH_3)_2)_2$). $^{31}$P NMR ($CDCl_3$): δ 147.40 ppm. Anal. calcd. for ($C_{27}H_{53}N_2O_3PS$): 517, Found: MS 517 ($M^+$), 540 ($MNa^+$).

Synthesis of a Reverse Capture Probe Using W330

The DNA oligomers were synthesized using ABI 392/394 RNA/DNA synthesizers. One unit of W330 was incorporated into the oligomers using the same chemistry as for the nucleosides. After completion of the DNA synthesis, the W330 connected oligomer was treated with 10% diethylamine in acetonitrile on line with an end procedure "End-DEA Wash". DMT was removed on line using the synthesizer's "DMT OFF" function. The disulfide function was introduced during the basic deprotection-cleavage stage by using CT83 as shown in Scheme 2. The crude oligomers were purified on a Hitachi 7200 semi-preparative HPLC, using a CMS method "C6-10%35%100% fc27-37". The description of HPLC method is attached in Appendix 5. The concentrations of the DNA stocks were measured by UV absorbance. Detailed description of the reverse capture probe synthesis can be found in a separate Research History File. Three batches of a capture probe (D6105) were synthesized from 3 different batches of W330 (one capture probe per batch of W330). These capture probes were analyzed by Capillary Electrophoresis (CE) per SOP EQ037.04 and MALDI-TOF by HT Labs in San Diego.

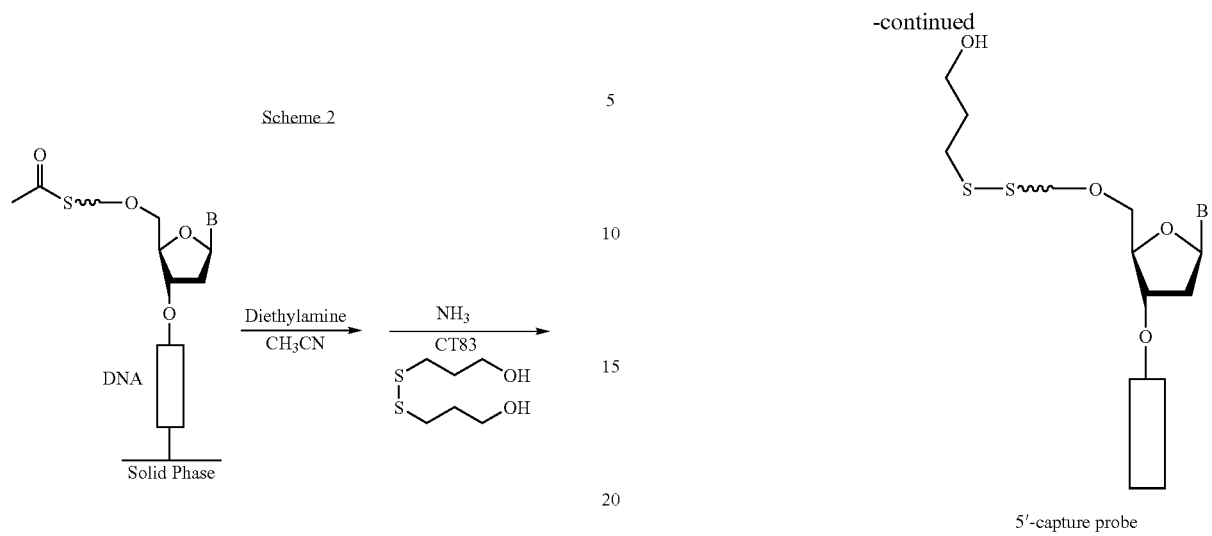

Cleavage of Reverse (5'-linker arm) Capture Probes and conversion to disulfide functionality

The invention claimed is:

1. An analog compound having formula (I):

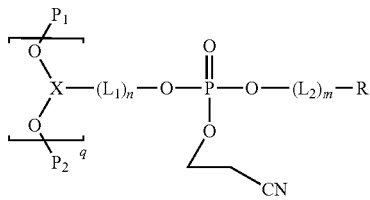

wherein
X is a backbone spacer;
t is 0 or 1;
R is a redox active moiety;
$L_1$ and $L_2$ are linkers;
n=0 or 1;
m=0 or 1;
wherein n+m is at least 1;
$P_1$ and $P_2$ are independently selected from the group consisting of hydrogen, phosphoramidite, a protecting group, and a nucleoside containing group, wherein at least one of $P_1$ and $P_2$ is said protecting group or said nucleoside containing group; and
q is greater than or equal to 1.

2. A compound according to claim 1, wherein said redox active moiety comprises a metallocene.

3. A compound according to claim 1, wherein said redox active moiety comprises a metallocene derivative.

4. A compound according to claim 2, wherein said metallocene is a ferrocene.

5. A compound according to claim 3, wherein said metallocene derivative is a ferrocene derivative.

6. A compound according to claim 1, wherein at least one of said protection groups $P_1$ or $P_2$ is dimethoxytrityl ("DMT").

7. A compound according to claim 1, wherein said backbone spacer X is a $C_3$ alkyl group.

8. A compound according to claim 1, wherein said linkers $L_1$ and $L_2$ are $C_1$ alkyl and n is 1 and m is 4.

9. A compound according to claim 1, wherein said backbone spacer is selected from the group consisting of alkyl and substituted alkyl.

10. A compound according to claim 1, wherein said linkers are selected from the group consisting of alkyl and substituted alkyl.

11. A compound according to claim 1, having the formula (II):

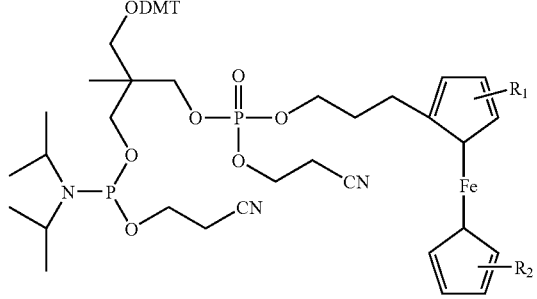

wherein $R_1$, are $R_2$ are independently selected from H and halogen.

12. A compound according to claim 11, wherein $R_1$ and $R_2$ are H.

13. A compound according to claim 11, wherein $R_1$ is H and $R_2$ is Cl.

14. A compound according to claim 11, wherein $R_1$ and $R_2$ are Cl.

15. A compound having the formula (III)

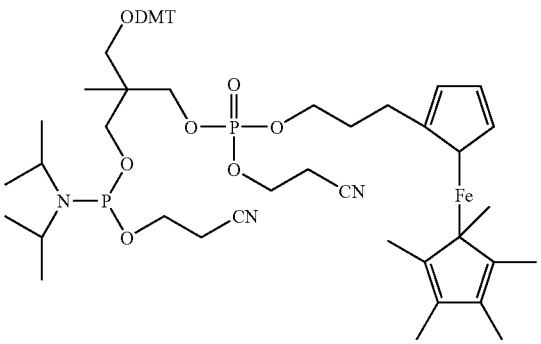

16. A composition comprising a compound according to any one of claims 1 to 15.

17. A nucleic acid derivative comprising a compound according to claim 1, wherein at least one of $P_1$ and $P_2$ is a nucleoside containing group.

18. A nucleic acid derivative according to claim 17, wherein both $P_1$ and $P_2$ are nucleoside containing groups.

19. A method of detecting a target nucleic acid comprising:
a) providing a substrate comprising:
   i) an electrode;
   ii) a self-assembled monolayer (SAM) on said electrode; and
   iii) a capture probe disposed on said electrode, wherein said capture probe binds to said target nucleic acid;
b) forming a complex comprising said capture probe, said target nucleic acid, and a label probe comprising the compound according to any one of claims 1-7 and 9-16, and
c) detecting electron transfer from a redox active moiety of said label probe to said conductive surface of said electrode to detect said target nucleic acid.

20. A kit comprising one or more members from the group consisting of a compound according to claim 1 and a nucleic acid derivative according to claim 17.

21. A compound of formula W330.

22. Compositions comprising W330 incorporated as a linker.

* * * * *

SEQUENCE LISTING

```
<160> NUMBER OF SEQ ID NOS: 3

<210> SEQ ID NO 1
<211> LENGTH: 11
<212> TYPE: DNA
<213> ORGANISM: Artificial
<220> FEATURE:
<223> OTHER INFORMATION: Synthesis of Non-Nucleotide Ferrocene Label

<400> SEQUENCE: 1
tccgtgtcca c                                                              11

<210> SEQ ID NO 2
<211> LENGTH: 11
<212> TYPE: DNA
<213> ORGANISM: Artificial
<220> FEATURE:
<223> OTHER INFORMATION: Synthesis of Non-Nucleotide Ferrocene Label

<400> SEQUENCE: 2
tccgtgtcca c                                                              11

<210> SEQ ID NO 3
<211> LENGTH: 15
<212> TYPE: DNA
<213> ORGANISM: Artificial
<220> FEATURE:
<223> OTHER INFORMATION: Synthesis of Reverse Linker Phosphoramidite

<400> SEQUENCE: 3
cgatagagtg ttcct                                                          15
```